(12) United States Patent
De La Huerga

(10) Patent No.: US 6,346,886 B1
(45) Date of Patent: *Feb. 12, 2002

(54) ELECTRONIC IDENTIFICATION APPARATUS

(76) Inventor: Carlos De La Huerga, 9190 North Upper River Rd., Milwaukee, WI (US) 53217

( * ) Notice: Subject to any disclaimer, the term of this patent is extended or adjusted under 35 U.S.C. 154(b) by 0 days.

This patent is subject to a terminal disclaimer.

(21) Appl. No.: 09/596,715

(22) Filed: Jun. 19, 2000

Related U.S. Application Data

(63) Continuation-in-part of application No. 09/200,881, filed on Nov. 30, 1998, now Pat. No. 6,255,951, which is a continuation-in-part of application No. 09/007,290, filed on Jan. 14, 1998, now Pat. No. 5,883,576, and a continuation-in-part of application No. 09/185,137, filed on Nov. 3, 1998, now Pat. No. 6,259,654, which is a continuation-in-part of application No. 08/832,613, filed on Mar. 28, 1997, now Pat. No. 5,852,590.

(60) Provisional application No. 60/033,491, filed on Dec. 20, 1996.

(51) Int. Cl.[7] ............................................. G08B 23/00
(52) U.S. Cl. ................... 340/573.1; 340/573.4; 340/572.8; 340/825.06; 340/825.15; 340/825.17; 340/5.8; 340/5.81
(58) Field of Search ................... 340/573.1, 573.4, 340/572.8, 572.9, 825.49, 5.8, 5.81, 10.51, 825.06, 825.07, 825.15, 825.16, 825.17

(56) References Cited

U.S. PATENT DOCUMENTS

| | | | | |
|---|---|---|---|---|
| 4,885,571 A | * | 12/1989 | Pauley et al. ............ | 340/573.1 |
| 5,204,670 A | * | 4/1993 | Stinton .................... | 340/10.42 |
| 5,455,851 A | * | 10/1995 | Chaco et al. ................. | 379/38 |
| 5,493,805 A | * | 2/1996 | Penuela et al. .............. | 40/633 |
| 5,504,474 A | * | 4/1996 | Libman et al. ........... | 340/572.1 |
| 5,525,969 A | * | 6/1996 | LaDue .................... | 340/573.4 |
| 5,532,705 A | * | 7/1996 | Hama ........................ | 343/718 |
| 5,742,233 A | * | 4/1998 | Hoffman et al. .......... | 340/573.1 |
| 5,877,675 A | * | 3/1999 | Rebstock et al. ....... | 340/286.07 |
| 5,883,576 A | * | 3/1999 | De La Huerga ......... | 340/573.1 |
| 5,936,529 A | * | 8/1999 | Reisman et al. ......... | 340/573.1 |
| 6,104,295 A | * | 8/2000 | Gaisser et al. ........... | 340/573.4 |
| 6,140,936 A | * | 10/2000 | Armstrong .................. | 340/5.6 |
| 6,255,951 B1 | * | 7/2001 | De La Huerga ......... | 340/573.1 |

* cited by examiner

*Primary Examiner*—Daniel J. Wu
*Assistant Examiner*—Toan Pham
(74) *Attorney, Agent, or Firm*—Quarles & Brady, LLP

(57) ABSTRACT

An electronic identification apparatus having data storage memory on board a removable transceiver device. The transceiver device also includes a processor and a transponder for receiving information pertaining to the object/person to which it is attached and storing the information in memory. The transceiver also transmits stored data to a control computer or the external devices. The transceiver is mounted on a base, such as a wristband, and the apparatus includes an attachment sensor indicating whether the transceiver is attached to the base. If the transceiver has been removed from the base, the processor performs one or more lockdown operations to prevent the stored data from being used in connection with another object or person. The lockdown operations include clearing the contents of the memory, disabling access to the memory, suppressing the display of stored data and activating an alarm.

165 Claims, 16 Drawing Sheets

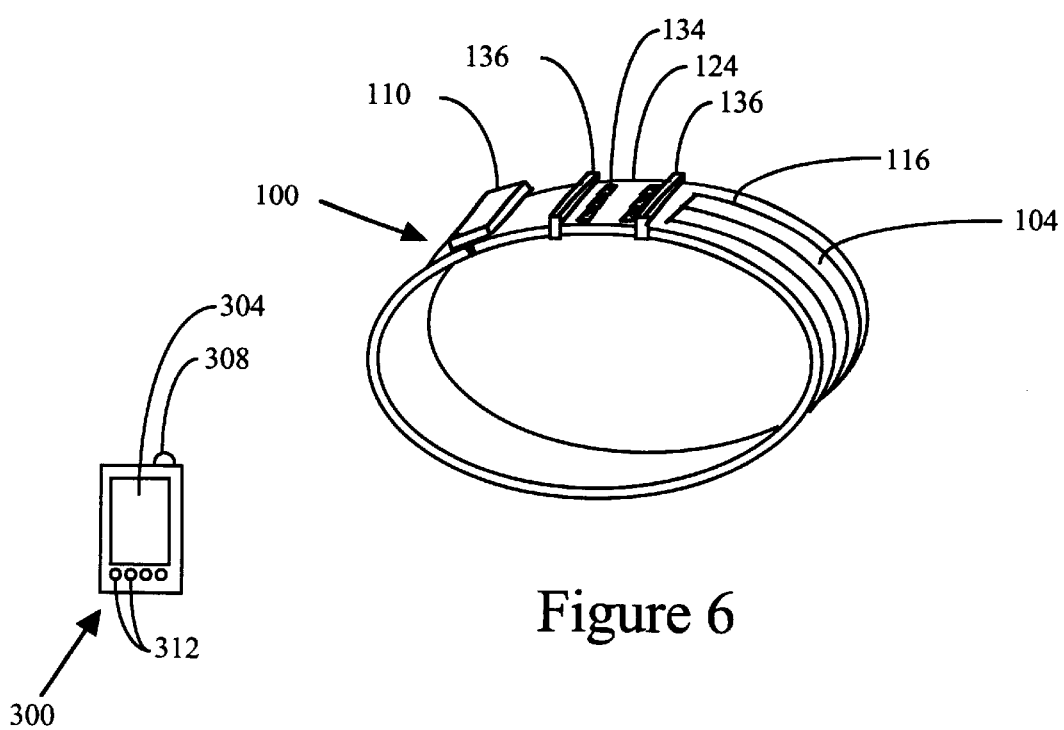
Figure 6
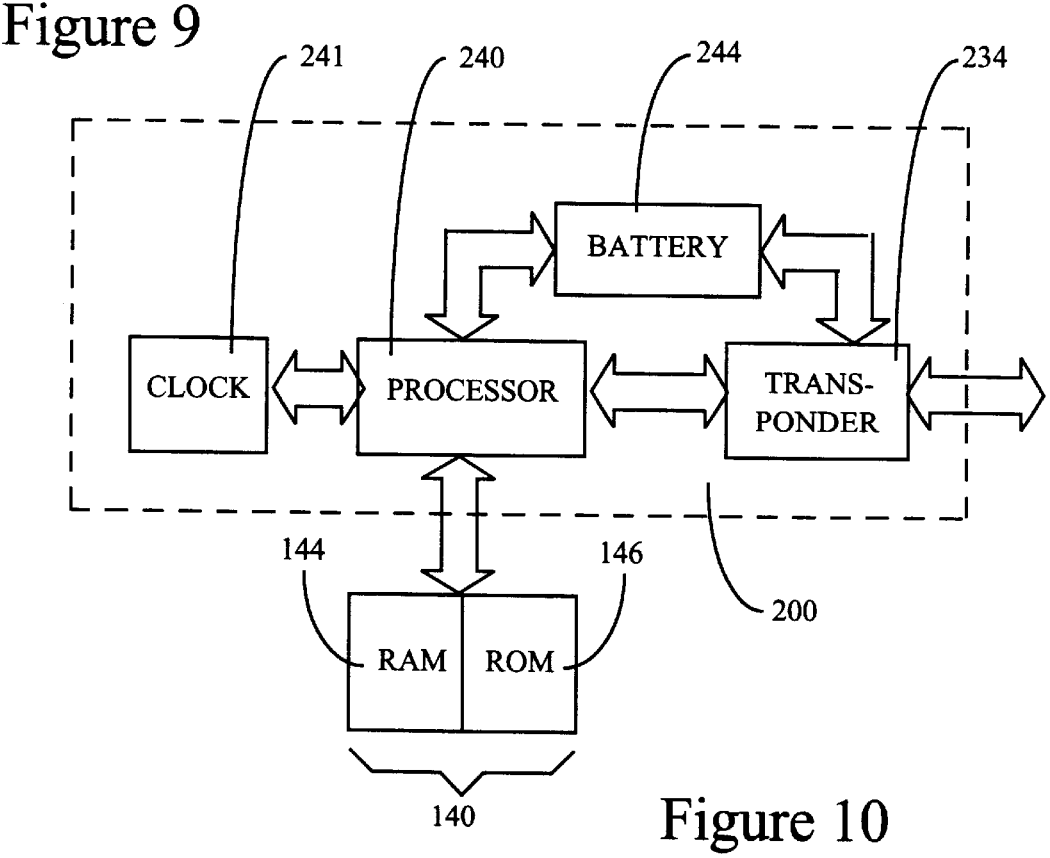
Figure 9
Figure 10

ELECTRONIC IDENTIFICATION APPARATUS

CROSS-REFERENCE TO RELATED APPLICATIONS

This application is a continuation in part of U.S. patent application Ser. No. 09/200,881 filed on Nov. 30, 1998, now U.S. Pat. No. 6,255,951 and entitled "Electronic Identification Bracelet" which is a continuation in part of Ser. No. 09/007,290 U.S. Pat. No. 5,883,576 filed on Jan. 14, 1998 and entitled "Identification Bracelet With Electronic Information" and is also a continuation in part of U.S. patent application Ser. No. 09/185,137 filed on Nov. 3, 1998, now U.S. Pat. No. 6,259,654, and entitled "Multi-Vile Medication Organizer and Dispenser" which is a continuation in part of U.S. patent application Ser. No. 08/832,613 filed on Mar. 28, 1997, now U.S. Pat. No. 5,852,590, and entitled "Interactive Label for Medication Containers and Dispensers" which was originally filed as a provisional U.S. patent application Ser. No. 60/033,491 on Dec. 20, 1996.

STATEMENT REGARDING FEDERALLY SPONSORED RESEARCH OR DEVELOPMENT

Not applicable.

BACKGROUND OF THE INVENTION

The present invention relates to identification bracelets and more particularly to a disposable bracelet having an embedded electronic memory and a reusable transceiver which is releasably attachable to the bracelet for receiving data from a remote source to be stored in the memory and transmitting data stored in the memory to a remote receiver.

Throughout time accurate patient identification has been a paramount concern in administering medication to, and performing medical procedures on, a patient. Years ago patient identification was relatively simple as local doctors would provide all types of medical care for essentially every person within a small community and knew each patient personally.

However, in today's medical environment, patient identification is a much more arduous task for many reasons. First, literally hundreds of patients are examined and treated on a daily basis in large modern medical facilities, each doctor or nurse interacting with as many as twenty or more patients within a single day. With such high traffic unaided positive patient identification is nearly impossible for any doctor or nurse.

Second, many medical facilities are expansive including specialized departments which are spread out throughout the facility, many departments being on different floors or even in different buildings. For example, diagnostic examination, imaging, surgery, recovery, etc., areas are all usually separate and staffed by different personnel. As a patient is moved from one department to another, even if personnel within one department can visually identify a patient, personnel in another department may not be able to identify the patient.

Third, many patients are admitted into a medical facility for a period which is longer than a single shift. Where facility personnel changes during a patient's stay, unaided patient identification would be nearly impossible.

Fourth, in many cases medical personnel cannot rely on a patient for correct identification. Some patients might be experiencing severe trauma, be under the influence of medication or be asleep, thereby making positive identification verification impossible.

For years the standard for patient identification has been to place an identification bracelet on each patient's wrist. One bracelet includes a clear plastic sleeve having first and second ends and a paper strip. Information including a patient's name, an identification number and perhaps primary appearance characteristics (e.g. eye color, hair color, height, weight, etc.), are printed on a viewing surface of the strip. The strip is inserted in the sleeve with the viewing surface observable through the sleeve. The two ends of the sleeve are integrally joined using a mechanical fastener thereby forming a ring around the patient's wrist. These bracelets are designed to be removed only by cutting so that once a bracelet is placed on a patient, the bracelet cannot mistakenly be placed on another patient. In addition, these bracelets are inexpensive enough that they are disposable.

While these bracelets are helpful, often it is difficult to read information from the paper strips within the sleeves as the sleeves often hinder viewing, the paper strips slide inside the sleeve and can even become folded or crimped within the sleeve.

Recently, new plastic materials and new printing methods have been developed which enable printing directly on plastic surfaces. In addition, new adhesives have been developed which are used to fasten bracelet ends together. This new technology has facilitated single piece bracelets wherein identification material is printed directly on a viewing surface of a plastic strap and the strap is secured around a patient's wrist using an adhesive.

A patient's bracelet is used by all medical facility personnel to identify a patient. Prior to administering a medication a nurse or doctor reads the patient's name from the bracelet and compares the patient's name with the name of the patient for whom the medication was dispensed. The patient's name is usually printed either on a medication order or on a paper enclosed with the medication in a container or bag.

In addition, prior to performing any medical or diagnostic procedure, facility personnel also use the bracelet to identify a patient. For example, a person recording an electrocardiogram (EKG) to be sent to a computerized storage system will often be instructed to provide, via a keyboard, a patient's name and identification number from the bracelet. Both the name and number are often requested as a misspelling of the name is a fairly common mistake and the identification number provides redundant identification.

For the purpose of this explanation, printed plastic bracelets will be described as printed bracelets. While printed bracelets have improved identification, printed bracelets have a number of important shortcomings. First, only a small amount of information can be printed on a bracelet. In this regard, unless a person viewing identification information has a medical history file in his/her possession, the person cannot identify immediate medical status of a patient (e.g. medication to be administered, time to administer medication, recent medical procedures, symptoms, etc.).

Second, information on a plastic bracelet cannot automatically be transferred to electronic instrumentation such as an EKG machine, an imaging machine, etc. where a medical instrument requires patient information, the information must be manually provided by facility personnel.

Third, each time a patient must be identified, the doctor, nurse or orderly identifying the patient must pick up the patient's wrist and rotate the wrist or the bracelet to a position wherein the identification information is observable. While this simple procedure is not in and of itself difficult for a person to perform or extremely bothersome to a patient; when the procedure must be performed a dozen or more times each day, the cumulative effect can be both bothersome to the patient and burdensome to the person who has to identify the patient.

Fourth, once information has been printed on the bracelet, the information cannot be changed and additional information cannot be added. This may not be important during short stays at a medical facility because printed information likely will not change appreciably over a short period. However, during a long stay at a facility, some printed information, in particular primary appearance characteristics (e.g. weight, etc.), may change and therefore should be updated.

One way in which to transfer identifying information from a bracelet to a medical instrument is to provide identifying information in bar code form. Bar codes, however, also have short-comings. While a bar code provides a machine readable format, only a limited amount of information can be represented by a bar code. This is because bar codes typically require as much space per represented character than the conventional alphabet. While smaller codes are possible, smaller codes are extremely difficult to read. In addition, practically, only a certain length of bar code is possible given the natural curve of a patient's wrist and the requirement that the code be essentially flat during scanning. In addition, like conventional printing, bar codes cannot be modified and therefore bracelet information cannot be modified after a bar is printed. Because a bar code cannot be read unless it is essentially flat, a bar code, to a greater extent than conventional print, requires special placement of a patient's wrist to read represented information. Furthermore, non-contact bar code reading devices are relatively expensive and often it takes several attempts to read a code accurately.

U.S. Pat. No. 5,493,805 describes an identification device including a memory "button" or chip which may be embedded within a bracelet, the bracelet worn by a patient. Identification information is electronically stored in the chip and can be accessed by use of a hand held instrument, preferably by simply touching the chip with a probe or the like. In addition to the electronically stored information, basic patient information can be printed on the bracelet for visual observation by a person. Preferably, the chip has a robust construction so that it is removable from the bracelet without being damaged and is then erasable, sterilizable and reusable to identify another patient. However, despite the chips robust construction, this patent contemplates that the chip might be disposable after a single use. Chip disposal is preferred over reuse as reuse might be perceived as unsanitary and may therefore be objectionable. This is particularly true where a patient has a communicable disease or expires while wearing a bracelet. For the purposes of this explanation, a bracelet including a simple memory chip will be referred to herein as a memory chip bracelet.

Memory chip bracelets overcome many of the problems associated with printed bracelets. For example, assuming a well designed memory chip, memory chip bracelets facilitate storage of a relatively large amount of information. In addition, memory chip bracelets facilitate modification of stored information. Moreover, memory chip bracelets facilitate transfer of information from the chip by simply touching the chip via a probe.

Unfortunately, memory chip bracelets also have several shortcomings. First, as with printed bracelets, identifying a patient wearing a memory chip bracelet still requires a doctor, nurse or orderly to position the chip in some orientation where good chip contact can be made. Because a memory chip includes a relatively large amount of information, in many cases the chip will be used more often than printed identification information to access needed information. For example, with a printed bracelet, the bracelet is used only to identify a patient and other information about the patient is usually accessed from some other source (e.g. a computer or a patient file).

With a memory chip bracelet, medicine administration history, treatment history, symptoms, diagnostic history, etc., may all be stored on the chip. Upon entry into a patient's room, the chip may be used once for identification and a second time for medicine or treatment history or to retrieve some other information. The chip may be used one or more additional times to access other information. Repeated chip readings are burdensome.

Second, where memory chips are reusable, despite sterilization there could still be a perception of unsanitary conditions rendering reusable chips objectionable.

Third, where memory chips are reusable, there is a possibility that chip information might not be erased or may only be partially erased prior to being used to identify another patient. Such a mistake could lead to erroneous identification and ultimately to incorrect treatment or diagnosis.

Fourth, chip removal, erasing, sanitizing, reinsertion into a new bracelet and rewriting to identify another patient is a burdensome and relatively expensive procedure, the cost and bother of which probably is not justifiable during all medical facility visits. For example, a ten minute visit probably would not justify such a costly and time consuming procedure.

The U.S. Pat. No. 5,493,805 patent also contemplates a bracelet wherein the chip includes an integral antenna for transmitting information to a hand held device. The preferred transmitter is a radio frequency transmitter wherein an external coil generates a field which provides energy to the chip within the field for transmitting information to the hand held device. Another chip embodiment might include a transmitter and a separate power source (e.g. a battery) providing power to the transmitter for transmitting information. For the purposes of this explanation, bracelets including a transmitter embedded in a chip will be referred to as transmitting bracelets.

Transmitting bracelets eliminate the need for reorienting a bracelet or a patients arm to access information from a chip. However, even transmitting bracelets have several shortcomings. First, while a memory on a chip may be inexpensive, transmitting circuitry on a chip increases chip costs appreciably. While bracelet costs may be defrayed by reusing the transmitting chip as indicated above, even after sterilization, reuse might be perceived as unsanitary and might therefore be objectionable. For these reasons, relatively expensive transmitting bracelets may only be justifiable in instances where a patient is admitted for an extended period and printed bracelets may be more suitable under other circumstances.

Second, as with memory chip bracelets, where a transmitting chip is reused, there is always the danger that a portion of the memory might not be erased prior to rewriting and patient identification or information could be confused.

Third, if a bracelet is designed properly, it is difficult to remove a chip from a bracelet. In patient identification, it is important that a chip be attached to the bracelet so that it cannot inadvertently be removed, dislodged or replaced. If a chip is to be reused, the chip has to be removed despite integral attachment. For this reason, a chip must be securely lodged within and integral with the bracelet to prohibit inadvertent removal. Integral attachment makes removal difficult at best and may require special tools (as recognized in the U.S. Pat. No. 5,493,805 patent), further increasing identification system costs.

Fourth, where a chip has to be removed from a bracelet for sterilization, the chip could be damaged or even destroyed during removal, rendering the chip useless. While damaged memory chips might be inexpensive and therefore disposable, damaged transmitting chips represent appreciable cost.

Fifth, in the alternative, instead of removing a chip from a bracelet, the entire chip and bracelet could be sterilized and the chip erased for reuse. It is even more likely, however, that this option would be perceived as unsanitary. In addition, while the chip could be erased and rewritten, printed identification information on the bracelet could not be easily erased and reprinted.

Sixth, a transmitting chip may be damaged in certain environments. For example, such a chip might not be waterproof and therefore would be damaged during bathing. In addition, a transmitter chip may be susceptible to magnetic or electric fields (e.g. MRI) within a medical environment. Similarly, a transmitter chip might give off a field of its own which could interfere with diagnostic or treatment fields.

Seventh, during extended hospitalization periods, a chip battery might need to be replaced. Replacing a battery while a bracelet is attached to a patient would be difficult at best.

When bathing, within a treatment or diagnostic energy field, or to replace a battery, a bracelet could be removed. However, removal is undesirable because a removed bracelet could be confused with another bracelet. In addition, because bracelets are constructed so that they cannot be easily removed, usually a bracelet would have to be destroyed to be removed.

Moreover, it is contemplated that during a stay at a medical facility, only rarely is it necessary to remove a patient's identification bracelet and therefore, if removed, typically removal is inadvertent and unintended. Currently no system is known for indicating when a medical bracelet is inadvertently removed despite the need for patient identification at all times.

Eighth, a bracelet which includes a transmitter assembly is often relatively bulky. For example, see U.S. Pat. No. 5,793,290 which describes one wrist band transmitting device. Unfortunately, while a bulky device may not be objectionable to a relatively healthy and strong patient, many patients are relatively unhealthy and relatively weak. This is particularly true in the case of patients who remain in a facility for a long duration. Other generally weak facility occupants include infants and small children. For these patient types a bulky transmitter assembly is uncomfortable and generally objectionable.

For all of the reasons discussed above, it would be advantageous to have a patient identification mechanism which is inexpensive, disposable, rewritable, permanent during a patient's stay at a medical facility and accessible without reorienting a patient or the bracelet.

BRIEF SUMMARY OF THE INVENTION

In one embodiment the present invention includes an identification bracelet which includes a plastic strap having first and second ends, an electronic memory device (e.g. a silicon chip), a securing means for securing the first and second ends together around a patient's wrist and a transponder. The memory device is integrally embedded in the strap and cannot be removed from the strap without destroying the device. The transponder includes circuitry which can receive information from and transmit information to remote hand held electronic devices or the like. The transponder is releasably attachable to the bracelet adjacent the memory device. When attached to the bracelet, the transponder makes contact with the memory device and can receive information from, and provide information to, the memory device.

The bracelet, including memory device, is inexpensive and completely disposable. The transponder is relatively expensive. However, the cost of the transponder is defrayed because the transponder can be sterilized and reused. A processor for use with the transponder can either be a portion of the transponder assembly and hence reusable or can be integrally secured to the strap and hence disposable along with the inexpensive memory device.

One object of the invention is to provide an identification mechanism which can provide a large amount of information about a patient. To this end, in addition to a patient's name and identification number and primary appearance characteristics, the memory device of the present invention can store a patient's complete medical history if desired.

Another object of the invention is to provide a system for identifying patient's which allows remote gathering of information from a patient. A related object is to allow patient identification without physically touching a patient to reorient an identification bracelet or a patient's arm. With the transponder linked to the memory device, the transponder can access memory information and transmit the information to a remote electronic gathering device.

In addition to having an embedded memory device, the strap may also include a viewing surface on which basic identification information including name, identification number, etc., is printed.

One other object is to provide a single identification system which can be used to identify all patient's in a medical facility. When a patient first enters a hospital, the patient can be provided with a bracelet including a viewing surface and a memory device. Basic information can be printed on the viewing surface while basic information and other more detailed information (if available) can be written to the memory device. If the patient does not remain in the hospital for a long time, a transponder is never attached to the bracelet. During the patient's short stay, the printed information alone is used for identification. When the patient leaves the hospital or shortly thereafter, the bracelet can be removed and discarded.

However, if the patient remains in the hospital for an extended period or will be undergoing extensive review or treatment during a short period, a transponder can be attached to the bracelet and linked to the memory device so that information thereon can be transmitted and altered to reflect recent medical history. Thus, the releasably securable transponder may or may not be utilized, depending on the circumstances.

Another object is to meet the aforementioned objects yet provide a relatively inexpensive identification system. To this end, when a patient's stay in a hospital is short, the identification bracelet comprises only the plastic strap and the embedded chip. The expensive transponder circuitry is not necessary. In addition, to reduce costs, where a transponder is used and prior to a patient leaving a hospital, the relatively expensive transponder can be removed and sterilized. The inexpensive bracelet and memory device can be discarded. Thus, in many cases the relatively expensive transponder is not needed and, even where a transponder is required, the transponder can be sterilized and reused.

Another object of the invention is to provide an identification system wherein memory is never reused so that erasing and rewriting errors never occur. To this end, no matter what, after a memory device is used to identify one patient, the same memory device is never reused to identify a second patient.

In one embodiment the memory includes both a read only memory (ROM), which can be written to once and then only read, and a random access memory (RAM) which can be written to, erased and rewritten to several times. In this case, it is contemplated that basic identification information like a name and an identification number will be written to the ROM once and thereafter cannot be altered. Other information will be written to the RAM and can later be altered as treatment, conditions, or diagnosis changes. For example, information stored in the RAM can be changed to reflect a patient's current weight should weight change during a long hospital stay or to reflect a procedure to be performed on the patient.

Yet another object is to provide an identification device wherein basic information is unalterable but other information could be altered to reflect changes in treatment, diagnosis, etc. The RAM/ROM mix of memory facilitates this object.

Yet another object is to record the time when the transponder is removed from the bracelet. This can be done by recording the time to memory every minute, therefore the last recorded time is within 1 minute of the time the transponder was removed. The time of removing the transponder can also be recorded by the transponder detecting via a pressure switch or a conductive path being opened that it is being removed from the bracelet and then writing the time to the memory prior to the transponder being completely removed.

In another embodiment a conductive loop is provided in a strap which when the strap forms a loop around a patient's wrist (or some other object), forms a short or closed circuit about the wrist such that the strap cannot be broken or cut without opening the short circuit. The processor is linked to the conductive loop to sense when the circuit is opened. When the circuit is opened the processor generates an alarm signal. Preferably, the alarm signal either causes an alarm indicator (e.g. an audible alarm) which is linked to the processor to indicate an open circuit or is transmitted via the transmitter to a receiver proximate the patient's location which in turn notifies an attending physician (e.g. desk nurse or the like) that the strap has been cut. The preferred system includes the latter and is undetectable by the patient so as not to startle the patient.

Similarly, preferably, when a transmitter assembly is removed from the strap inadvertently, the processor generates an alarm signal to indicate inadvertent removal. On one hand, the processor may be part of a transponder assembly, which includes an alarm indicator (e.g. audible alarm) for indicating removal. In the alternative, when the processor generates an alarm signal, the transponder may transmit an alarm signal to an external receiver device in the patient's vicinity to notify an attending physician. On the other hand, the processor may be secured to the strap. In yet another embodiment, the processor may routinely and periodically generate an identification signal which is provided to a monitoring device, when the conductor is cut or the transmitter assembly is removed the identification signal is not provided, thus indicating a cut or removal.

In each embodiment where inadvertent strap cutting and transponder removal cause the processor to generate an alarm signal, a deactivation device may be provided to deactivate the processor so that the processor does not generate an alarm signal when the strap is cut or when the transponder is removed.

Thus, another object of the invention is to provide an identification device for which inadvertent removal is sensed. The conductive member and processor together provide such a system.

In yet another embodiment, an indicator is linked to the processor for indicating when a processor is active. Thus, when a physician uses a handheld device (HHD) to communicate with an identification bracelet processor, the processor which receives a query from the HHD indicates reception via the indicator and may indicate other activity (e.g. processing or transmission in a similar fashion).

Thus, one other object is to enable a physician to ensure that even where two or more identification bracelets are proximate an HHD, the physician is receiving data from an intended device. Where more than one identification device is proximate an HHD and the HHD is used to query one of the devices, a device receiving a query and processing to respond thereto indicates processing via the indicator (e.g., audible or visual indicator). The physician can identify the responding device via the signal. Where an unintended device or more than one device responds, the physician can break communication and then reinterrogate after taking steps to ensure that the intended device responds (e.g. repositioning the HHD).

The invention is also useable to provide a secure facility or as part of a security system. For example, medical facilities generally have recognized the need for systems to ensure that infants and children are not abducted. With the present invention and, in particular, the embodiments including a strap, an inventive device can be secured to an infant/child which, when tampered with, indicates tampering via an alarm signal of some type (e.g., an audible or visual indication, indication at a nurses station, etc.)

In addition, in the context of a security system, the inventive device may indicate device tampering in any of several different ways. For example, the device may only be able to transmit an identification signal when the device has not been tampered with. In this case, a monitoring system tracks an identification signal from the device and is programmed to expect an identification signal periodically from the device. When an expected signal is not received, the system is programmed to assume tampering and indicates tampering when a signal is not received. Thus, absence of an expected signal is considered a signal for the purposes of the present invention. In the alternative, the device may only generate an identifier signal when tampered with.

In another embodiment of the invention the identification bracelet is comprised of a strap that does not have the embedded memory chip. In this embodiment a reusable transponder is attached to the bracelet, the transponder now including the memory chip to store information about the patient. The transponder senses when it is attached to the strap by a sensor. The sensor may include a first sensor coupled to the transponder and a second sensor coupled to the strap or any other base member to which the transponder is attached. The sensor may be a button, conductive circuit, optical circuit, magnetic sensor or any other sensing device known in the electronic arts. The memory in the transponder is programmed with patient information either before or after it is attached to the strap. Once attached the transponder monitors the sensor to determine if it is still attached to the strap. As long as it is attached to the strap the transponder may provide the patient information to other devices and may receive additional information to be stored in the memory. If the transponder is removed from the strap the transponder can perform one of several functions. In one case the transponder can automatically erase the information stored in the memory so that the transponder can be safely attached to the strap of another patient and reprogrammed with information for that patient. The process of erasing the memory can be performed when the transponder is attached to the strap of another patient, so information about the previous patient is maintained until the transponder is reused. In another case the transponder may retain whatever information is in the memory, but cannot be programmed with new information for another patient until the previous patient's information has been transferred to a separate computer system. In this case the transponder will also disable any attempt to read its contents until a special code is received. Similarly should the transponder include a visual display, the display will no longer display patient information after removal from the strap. This ensures that patient information for one patient cannot be used to identify another patient. In another case it can present an alarm, indicating the improper removal of the transponder unless the transponder has received a special code to disable such an alarm. In another case the transponder is attached to the strap in a tamper resistant manner, so that it can only be removed by noticeably damaging the strap or the transducer. In a further case the transponder can record the time of removal in the memory.

In another embodiment of the invention the bracelet is comprised of a strap with an integral transponder. The transponder includes a memory device to store patient information. In this embodiment the transponder will now include a sensor to detect that the strap continues to be attached to the patient. If the strap is no longer attached to the patient one of several different functions occur, the several different functions including: erasing the memory, prohibiting reprogramming and access to the memory until a special code is received and the information in the memory is transferred to another computer, activating an alarm, etc. Alternatively, the bracelet can be attached so that it cannot be unnoticeably removed.

In another embodiment of the above invention the transponder can include a transducer to detect and record to the memory parameters regarding the patient wearing the transponder or the patient's environment. For example if the strap is firmly attached to the patient the transducer can detect the patient's heart rate by detecting mechanical or acoustic movement of blood through an artery and then recording the heart rate to the memory. Alternately an auxiliary medical device can be attached to the transducer to provide measurements about parameters regarding the patient or their environment. For example a non-invasive blood pressure device can measure the patient's blood pressure and transfer the measurement to the transponder via a cable or wireless transmission to be recorded in the memory.

In another embodiment of the invention the bracelet also comprises a strap with a memory chip permanently attached to it. To the strap may be attached a sensing transducer that can sense patient parameters (e.g. heart rate, pulse oximetry) for the patient to which the strap is attached or about the environment (e.g. temperature) of the patient and write them to the memory. The sensing transducer can include a remote sensor that is connected to the strap making contact with the memory. The sensing transducer need not include a transmitter to transmit the contents of the memory chip to a remote electronic gathering device as previously described. The memory can be linked to a conductive loop or conductive member in the strap as previously described so that removing the bracelet from the patient causes the memory to no longer function. This embodiment allows for the recording of parameters in a manner such that the stored parameter readings can only be associated with the patient and no other. The stored parameter readings in the memory chip can be read by removing the transducer and placing a reading device in contact with the electrical contacts of the memory chip or the transducer can include a transmitter that can send the parameter readings to a remote data gathering device. Preferably, the parameter readings include the time they were recorded.

In another embodiment of the invention the transponder is equipped to transfer information to and receive information from other devices via personal area network wireless (PAN) communications. A PAN uses low power capacitive coupling to transfer information from a device closely associated with the patient's body, but not necessarily touching the skin, such as the bracelets described above. Using PAN technology, the patient information can be transferred to medical devices merely by placing a transducer near the body or by placing an electrode or transducer in contact with the body. The biomedical devices are designed to allow patient information in the form of PAN signals to be received and processed. A significant advantage of this method of communicating is that these medical devices do not need an auxiliary reading device to receive the patient information. Another advantage is that the biomedical devices can automatically detect when they are being used on a new patient, as the received patient information will immediately differ from the previously received information.

The present invention also includes an electronic information apparatus for use with an object data device that stores information related to an object. In this regard, the invention includes an apparatus comprising a base member having a connector for attaching the identification apparatus to the object and a processor assembly including a housing linkable to the base member, a memory for storing information, a data reader for reading information from an object data device, and a processor linked to the memory and to the reader for receiving information from the reader and storing the information in the memory. Preferably, the object data device is a data card including an interface segment, and the reader is capable of reading data via the interface segment. The interface segment may be a magnetic strip, although other embodiments are contemplated including electronic contacts. To help align a magnetic strip with the reader, a "pass-through" slot may be provided on the processor assembly housing which, when a card is passed therethrough, automatically aligns the interface segment with the reader. All of the security functions described above are applicable to this concept.

The present invention also includes a content-identifying containment apparatus. The containment apparatus comprises a vessel forming a container volume having an opening, a closure member for closing the opening, a base member affixed to one of the vessel and the closure member having at least one latching device, a memory for storing information, a processor assembly having a housing including a second latching device configured so as to be receivable by the first latching device to secure the processing assembly to the base member and a processor linked to the memory for processing container control information, the processor assembly, vessel, closure member and base member each being apparatus components. The apparatus further includes a latch linked to one of the apparatus components. When the housing is attached to the base member, the latch is positioned with respect to the vessel so as to restrain the closure member when in a locked position and to allow the closure member to be moved when in an unlocked position. When the housing is attached to the base member, the processor is linked to the latch for controlling the latch. The memory may either be integral with the base member or integral with the processor assembly. Preferably, the latch is a solenoid.

While various apparatus are described above, the invention also contemplates a plurality of different methods to be used with the apparatus above and to be used with other types of apparatus which can accomplish similar functions.

These and other objects, advantages and aspects of the invention will become apparent from the following description. In the description, reference is made to the accompanying drawings which form a part hereof, and in which there is shown an embodiment of the invention. Such embodiment does not necessarily represent the full scope of the invention and reference is made therefor, to the claims herein for interpreting the scope of the invention.

BRIEF DESCRIPTION OF THE SEVERAL VIEWS OF THE DRAWINGS

FIG. 6 is a perspective view of the bracelet of FIG. 1 in a looped configuration, albeit without the transceiver attached;

FIG. 9 is a plan view of a hand held electronic information gathering device used with the inventive transceiver;

FIG. 10 is a block diagram of the electronics associated with the inventive bracelet;

DETAILED DESCRIPTION OF THE INVENTION

A. Hardware

Figure 1:
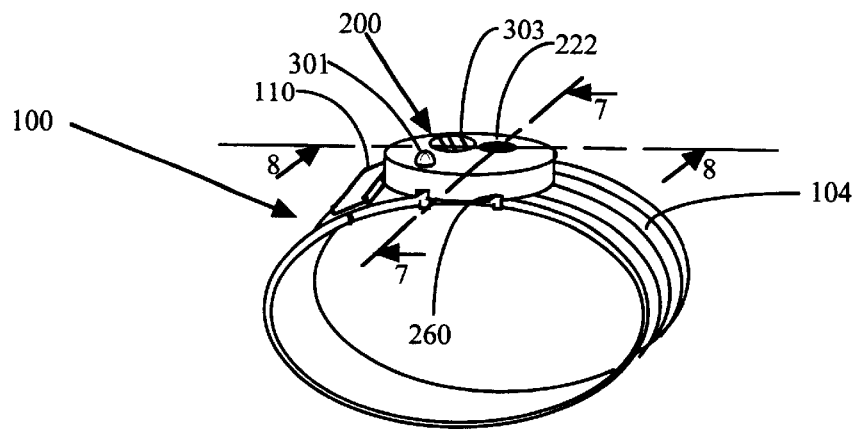
FIG. 1 is a perspective view of an inventive bracelet including a releasably attached transceiver.
Figure 2:
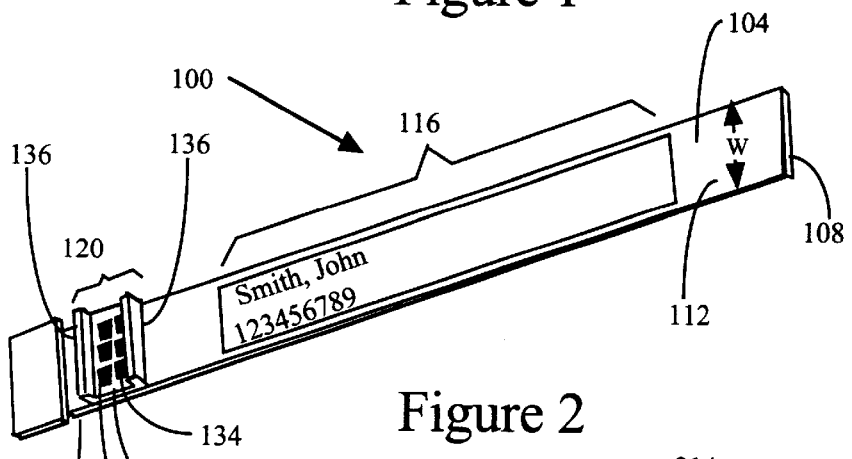
FIG. 2 is a perspective view of the bracelet of FIG. 1, albeit in a flat configuration prior to forming a loop and without the transceiver.
Figure 3:
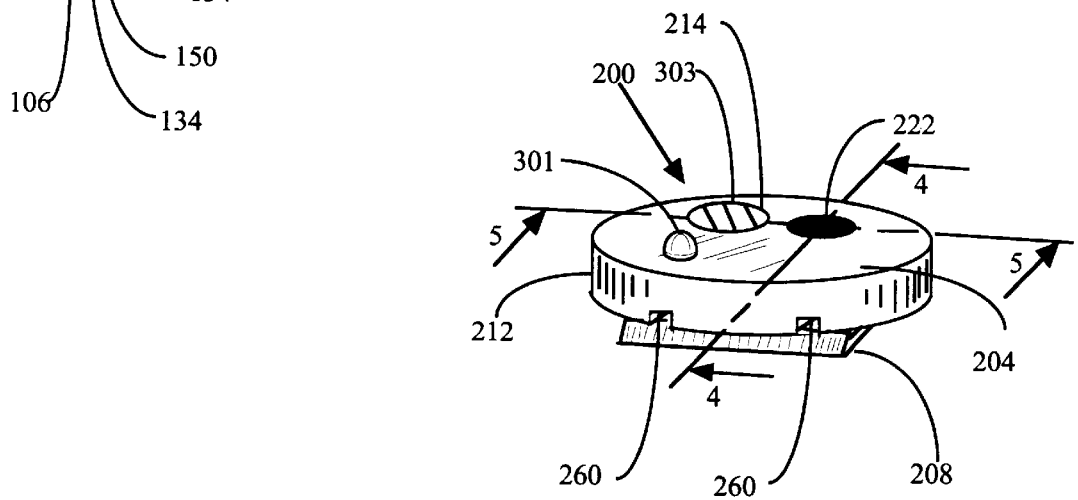
FIG. 3 is a perspective view of the inventive transceiver of FIG. 1.

Referring now to the drawings, wherein like reference characters represent corresponding elements throughout the several views, and more specifically referring to FIGS. 1, 2 and 3, the inventive identification assembly 100 generally includes a bracelet 104 and a communication device in the form of a transceiver 200. Bracelet 104 is preferably formed of a tear resistant plastic material and has first and second ends 106, 108, respectively. A clasp 110 is integrally connected to first end 106 and is constructed so that the clasp 110 can receive second end 108 and lock second end 108 relative to first end 106 forming a loop or ring (see also FIG. 6). To this end, it should be noted that any mechanism for securing ends 106 and 108 together is suitable. For example, the ends may be secured via adhesive, melting, crimping, etc.

Referring specifically to FIG. 2, bracelet 104 forms an identification surface 112 and includes two identification sections including a viewing section 116 and an electronic memory section 120. It is contemplated that basic identification information including a patient's name, an identification number and primary appearance characteristics (e.g. height, weight, hair color, etc.) would be printed on viewing section 116.

Figure 8:
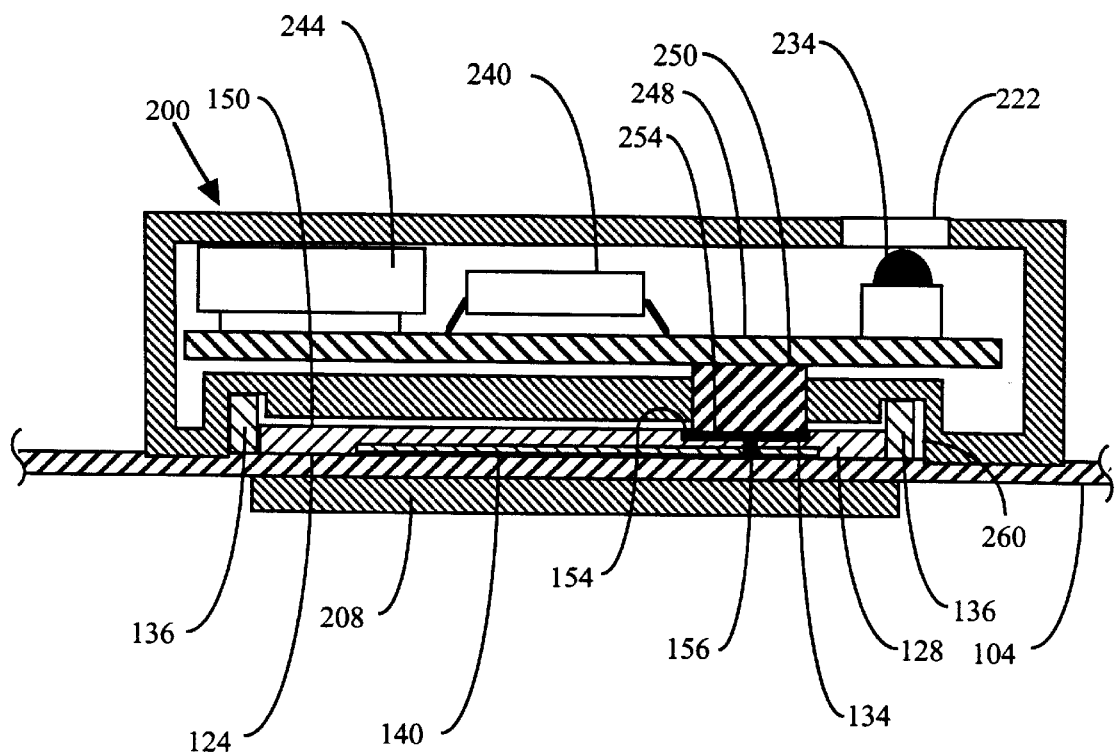
FIG. 8 is a cross sectional view taken along the line 8—8 of FIG. 1.
Figure 7:
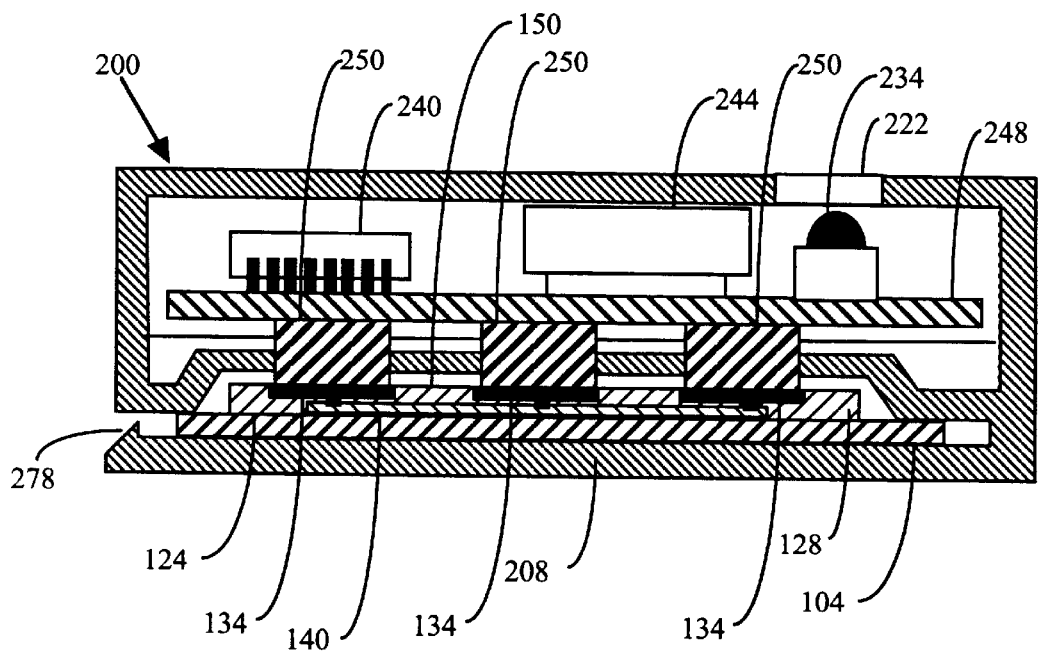
FIG. 7 is a cross sectional view taken along the line 7—7 of FIG. 1.

An electronic memory assembly 124 is provided at memory section 120. Referring also to FIGS. 7 and 8, assembly 124 includes a housing 128, a silicon memory device or chip 140, first and second electrical contact sets, each set including three electrical contacts, the contacts collectively referred to by numeral 134, and first and second guidance or alignment runners collectively referred to by numeral 136. Each set defines a line of contacts 134 which essentially traverses width W and the lines are parallel. Chip 140 can take any of several different forms as well known in the art. At a minimum, chip 140 must be configured to receive digital data via one or more chip inputs (not illustrated) and to provide data via one or more chip outputs (not illustrated). Referring to FIG. 10, preferably, chip 140 includes both a read only memory (ROM) 144 and a random access memory (RAM) 146. ROM 144 is only written to once and thereafter the information therein cannot be altered. RAM 146 can be written to many times and information stored therein can be altered.

In the illustrated embodiment, chip 140 comprises a flat wafer-like element which is centrally deposited within memory section 120. Housing 128 is formed of plastic, covers chip 140 forming an upper surface 150 and is bonded to identification surface 112 covering essentially all of memory section 120. Contacts 134 are exposed at distal ends 154 flush with upper surface 150 and extend down through housing 128 making electrical contact at proximal ends 156 with input and output terminals (not illustrated) on chip 140.

Runners 136 extend from identification surface 112 across a width W of bracelet 104, one runner on either side of housing 128, are parallel, are preferably formed from the same plastic used to form bracelet 104 and are integrally attached to or formed as part of bracelet 104.

Figure 4:
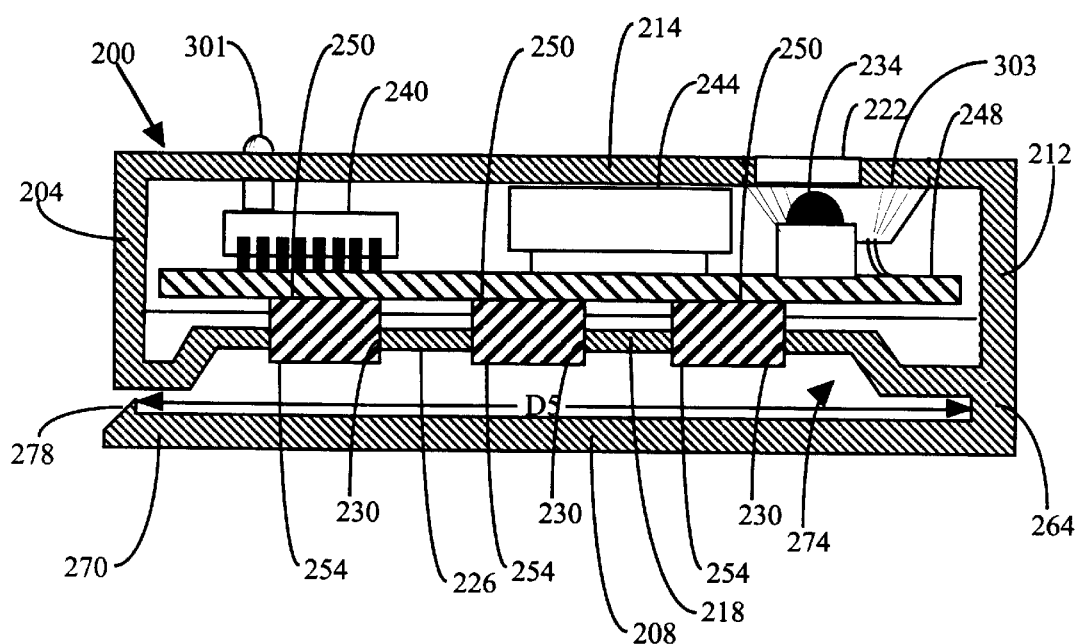
FIG. 4 is a cross sectional view taken along line 4—4 of FIG. 3.
Figure 5:
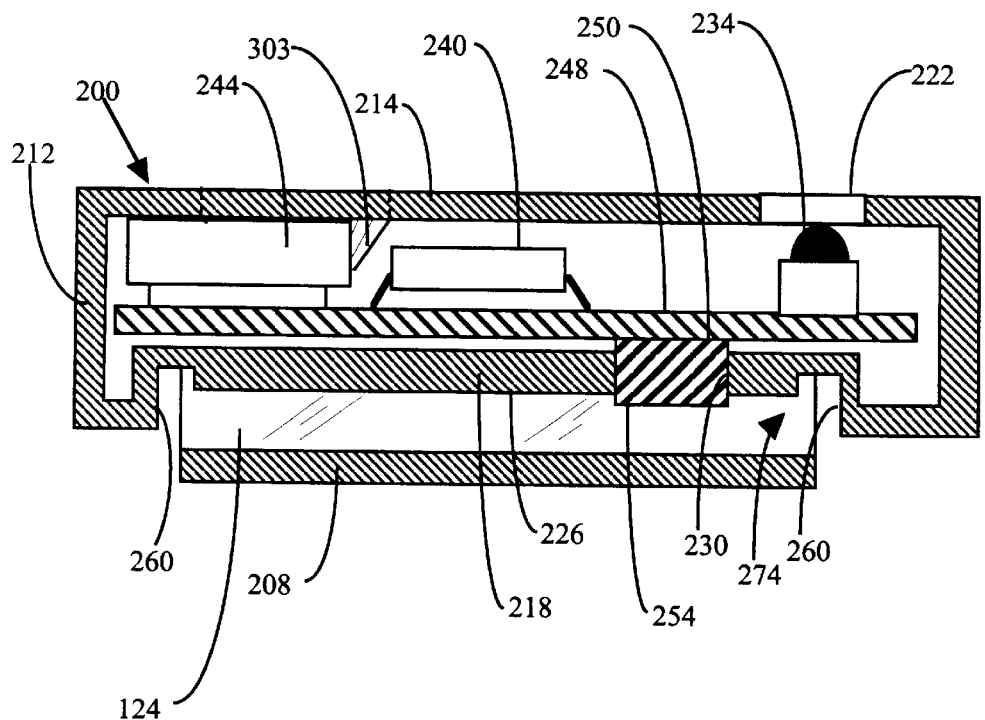
FIG. 5 is a cross sectional view taken along line 5—5 of FIG. 3.

Referring now to FIGS. 3, 4 and 5, among other things transceiver 200 includes a cylindrical transceiver housing 204 and a clip 208. Transceiver housing 204 includes a lateral cylindrical wall 212, a top wall 214 and a base wall 218. Top wall 214 forms a single optical opening or aperture 222. Base all 218 forms an undersurface 226 and three apertures collectively referred to by numeral 230. Apertures 230 are arranged in the same pattern as a row of contacts 134 (ee FIGS. 2, 7 and 8).

Referring to FIGS. 4, 5 and 10, an infrared transponder 234, a processor 240 and a battery 244 are all included inside transceiver 200 and are housed inside housing 204. Clock 241 can be an integral part of processor 240. A circuit board 248 is mounted inside transceiver housing 204. Transponder 234, processor 240, clock 241 and battery 244 are all mounted on circuit board 248. Transponder 234 is mounted just below optical opening 222 so that infrared signals can be received therethrough and transmitted therethrough. Battery 244 provides power to both processor 240 and transponder 234. Processor 240 is linked to transponder 234 for receiving information therefrom and providing information thereto.

Transponder 234 is capable of receiving and sending data via infrared signals and its operation should be well known to those skilled in the electronic arts.

Three electrical contacts are also linked to circuit board 248 and specifically to processor 240. Each of contacts 250 extends down through a separate one of apertures 230. Preferably, a distal end 254 of each contact 250 extends past undersurface 226. Contacts 250 are symmetrically configured to define a line of contacts.

Referring specifically to FIGS. 1, 3 and 5, undersurface 226 forms first and second channels or recesses collectively identified by numeral 260 on opposite sides of apertures 230. Channels 260 are parallel and spaced apart a distance equal to the distance between runners 136. Channels 260 are arranged with respect to contacts 250 such that when runners 136 are received within channels 260, contacts 250 are aligned with one of the lines of contacts formed by contacts 134.

Referring to FIGS. 3, 4 and 5, clip 208 includes an arm like member which has a proximal end 264 integrally connected to base wall 218 at one end of channels 260. Clip 208 extends from a proximal end 264 to a distal end 270 along the direction of channels 260 and is parallel to base wall 218. Thus, undersurface 226 and clip 208 together define a channel 274. A finger-like projection 278 extends from distal end 270 toward undersurface 226 but only traverses part of the distance between distal end 270 and undersurface 226. The distance D5 between proximal end 264 and projection 278 is at least as great as width W of bracelet 104.

Referring to FIG. 9, the inventive bracelet is meant to be used with a hand held data generating and receiving device HHD 300 which includes a display 304, a plurality of buttons for controlling the HHD 300 and an infrared transponder 308. Although not illustrated, HHD 300 also include a processor linked to each of buttons 312, display 304 and transponder 308 for controlling HHD operation. HHD 300, like transceiver 200, can generate and receive information via infrared signals. Thus, HHD 300 and transceiver 200 can communicate and exchange information.

B. Operation

In operation, the inventive patient identification bracelet can be used in several different ways for patient identification. It is contemplated that when a patient enters a medical facility to be examined or treated, initially a bracelet 104 like the one illustrated in FIG. 2 will be provided. To this end, a special printing and electronic writing device (not illustrated) is used to provide identifying information on the bracelet. The identifying information includes basic information (e.g. name, identification number, etc.) printed on identification surface 112 in the viewing area. In addition, the identifying information also includes the basic information and perhaps some other information which is electronically written to chip 140. To write to chip 140 the writing device includes electrical contacts which transmit data when they are placed in contact with contacts 134.

The basic information including name and identification number is written to the ROM while other information which might change during a patient's stay at the facility is written to the RAM so that information can be changed later if desired.

After an identifying bracelet 104 is provided, the bracelet 104 is looped around a patient's wrist (see FIG. 6) and clasp 110 is used to secure ends 106 and 108 together such that bracelet 104 cannot be removed from the patient's wrist without destroying the bracelet 104. Once bracelet 104 is placed around a patient's wrist, the bracelet 104 is not removed until the patient is leaving the medical facility. Thus, because the bracelet remains on the patient at all times, assuming correct information on the bracelet, bracelet information can be relied upon to perform proper patient identification.

When patient treatment or examination of a patient takes a short time, a bracelet without a transceiver is sufficient for identification purposes and therefore no transceiver is provided. To identify a patient, a person simply reads information from viewing section 116 in the conventional manner. In the alternative, a person having a special reading device could make electrical contact with contacts 134 and read information stored on chip 140.

However, when patient treatment or examination is extended or involves many facility personnel so that patient identification has to be performed many times during treatment or examination and identification becomes bothersome to a patient and tedious for facility personnel, a transceiver 200 is provided on bracelet 104 as illustrated in FIG. 1.

Referring to FIGS. 1 through 5, to attach transceiver 200 to bracelet 104, channel 274 is aligned with memory section 120 such that runners 136 are aligned with channels 260 and projection 278 is adjacent memory section 120. Then, memory section 120 is forced into channel 274 so that runners 136 are received within channels 260. Referring also to FIGS. 7 and 8, after memory section 120 is completely within channel 274, distal ends 254 of each contact 250 touch contacts 134 and are pressed thereagainst between undersurface 226 and clip 208. When so positioned, processor 240 can receive information from, or provide information to, chip 140 via contacts 250 and contacts 134.

Referring also to FIG. 9, with transceiver 200 firmly attached to bracelet 104 a doctor or nurse can use an HHD 300 to send infrared signals to transceiver 200. The infrared signals generated via HHD 300 should be of limited strength so that only a transceiver within a short range of the emitting device will receive the emitted signals. For example, signal strength might be limited such that only a transceiver within two or three feet of the HHD will receive emitted signals. For the purposes of this explanation, the term emitting range will be used to refer to the distance over which emitted infrared signals will be received via transceiver 200.

Referring still to FIG. 9 and also to FIGS. 7 and 8, to identify a patient, a doctor or nurse places HHD 300 within the emitting range of transceiver 200. The doctor then presses one of buttons 312 instructing HHD 300 to send a signal to transceiver 200 indicating that the transceiver should provide at least a subset of the information which identifies the patient and is stored on chip 140. After the appropriate button 312 is pressed, HHD 300 sends an infrared signal via transponder 308.

Assuming transceiver 200 is close enough to HHD 300 to receive the infrared signal, transponder 234 receives the signal and provides the signal to processor 240. Processor 240 decodes the signal, recognizes that the signal requests identifying information from chip 140 and accesses chip 140 via contacts 250 and 134. Once identifying information has been read from chip 140, processor 240 formats the information into a message for delivery to HHD 300. Next, processor 240 sends the message via transponder 234 and infrared signals to transponder 308. Assuming transponder 308 is still within the emitting range, transponder 308 receives the identifying message and displays the message via display 304 for the doctor or nurse to view. In addition, the HHD may store the identifying message for later retrieval or may correlate the identifying message with other information about the patient, thereafter displaying the correlated information in addition to patient identification.

During a patient's stay at a facility, transceiver 200 can be removed for any of a number of different reasons. For example, prior to bathing a patient transceiver 200 can be removed. In addition, transceiver 200 can be removed to replace a battery. Moreover, transceiver 200 can be removed prior to surgery or prior to placing a patient in a diagnostic or treatment field. In addition, if transceiver 200 becomes damaged it can be replaced. Importantly, in each of these cases, when transceiver 200 is removed, bracelet 104 remains on the patient's wrist. Thus, the patient is never separated from his/her identification information and the changes of incorrect identification are essentially negligible.

The time when transceiver 200 is removed from bracelet 104 can also be recorded to chip 140. This can be done by processor 240 obtaining the time from clock 241 and recording it to chip 140 every minute, therefore the last recorded time is within 1 minute of the time the transponder was removed. This time of removal can also be recorded by transceiver 200 detecting via a pressure switch or a conductive path being opened (see below) that it is being removed from the bracelet and then writing the time to chip 140 prior to transceiver 200 being completely removed.

In addition, medical history or future treatment information can be stored on chip 140 which can be accessed via HHD 300 or other medical equipment such as an imaging machine or a treatment machine equipped with a transponder and a processor. Moreover, information on chip 140 can be used in conjunction with diagnostic and treatment equipment to ensure that diagnostic and treatment procedures are not performed on incorrect patients. To this end, each diagnostic and treatment machine can be equipped with a transponder device for communication with transceivers 200. Like the HHD, prior to performing a diagnostic or treatment procedure on a patient, it is contemplated that the machine sends an interrogation message via its transponder to a patient's transceiver 200 requesting that the transceiver identify the patient. In response transceiver 200 sends back identifying information. The machine then compares received information with information correlated to the patient for whom the treatment or diagnosis was ordered. If the information received is identical to the correlated information, the machine initiates and performs the procedure. However, if the information is not identical, the machine indicates that there is no match and halts the procedure until a doctor or nurse can identify the discrepancy.

In addition to reading information from chip 140, processor 240 can also add information to the information already stored in chip 140 or can rewrite information thereby changing information in the RAM section of chip 140. To this end, HHD 300 can also be used to send additional information to transceiver 200 for updating or adding information to chip 140. When this type of information is received by processor 240 via transponder 234, processor 240 decodes the information and recognizes the information as updated or additional information to be stored on chip 140. Then processor 240 writes to chip 140 providing the updated or additional information.

After patient treatment and examination and before the patient leaves the medical facility, transceiver 200 can be removed from bracelet 104 by simply separating clip 208 from undersurface 226 and removed bracelet 104 from channel 274. Once transceiver 200 is removed, bracelet 104 can be removed from the patient's wrist by cutting and bracelet 104 can be discarded. Transceiver 200 is then sterilized and can be reused at a later time to identify another patient by clipping transceiver 200 on a different bracelet.

C. Alternative Embodiments

Figure 11:
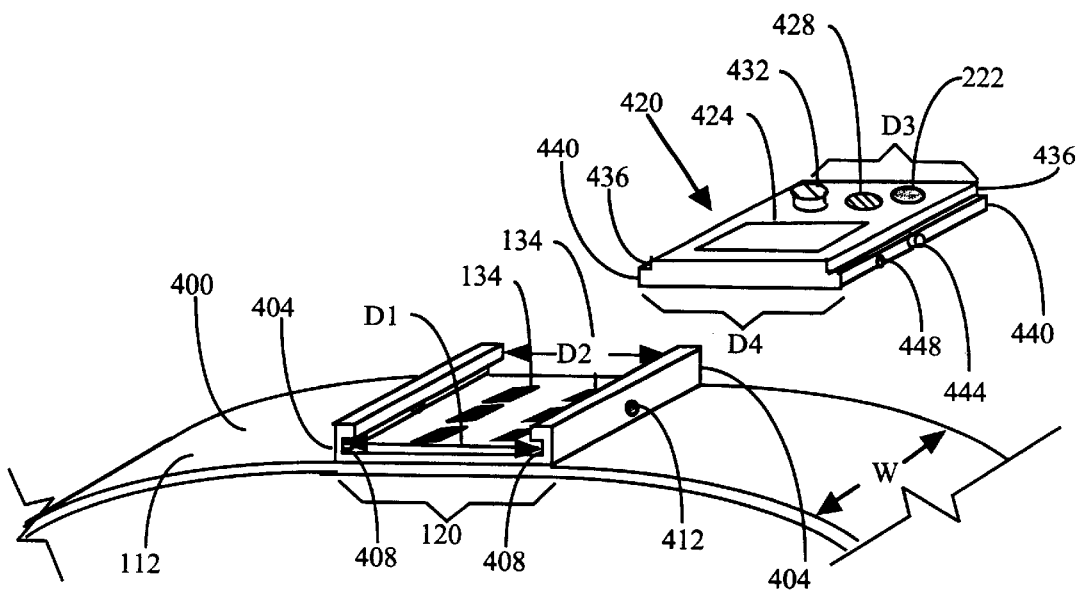
FIG. 11 is a perspective view of a second embodiment of an inventive identification bracelet with a transceiver disconnected from a bracelet strap.

Referring now to FIG. 11, a second embodiment of the present invention is illustrated. As with the first embodiment, the second embodiment includes a bracelet 400 and a detachable transceiver 420. Many components of this second embodiment are essentially identical in both form and function to the first embodiment and therefore will not be explained here again in detail. This second embodiment differs from the first embodiment in several ways.

Transceiver 420 includes several features which are not, but could be included, in the first embodiment. For example, in addition to the features described above, transceiver 420 includes a display 424, an indicator device 428 and a button 432. It is contemplated that display 424 might be an LCD linked to a transponder processor (similar to FIG. 10) for visually imparting patient identifying information.

Indicator device 428 is also linked to the transceiver processor, can take several different forms and can be used for any of several different purposes. For example, indicator device 428 can be an audio alarm which generates a loud buzz, beep or ring. In the alternative, indicator device 428 may be a visual alarm (i.e. light source) for emitting light. One application for indicator device 428 is to indicate when transceiver 420 has received a signal via transponder 234. Similarly, indicator device 428 could be used to indicate when transceiver 420 is transmitting a signal. To either of these ends, indicator device 428 can either generate an audio or a visual indicator signal updating transceiver status.

In addition, where the transceiver processor has interrogation capability, indicator device 428 may be used as an alarm. For example, one system is described above wherein a diagnostic or treatment machine interrogates a patient bracelet prior to performing a diagnostic or treatment procedure. Where a machine interrogates a bracelet and patient information transmitted by the bracelet is not identical to information corresponding to a patient for which the diagnosis or treatment was ordered, the machine will not perform the procedure until a doctor or nurse determines why the information did not match. Here, where the transceiver has interrogation capability, instead of the machine interrogating the transceiver processor, the processor may instead interrogate the machine.

It is contemplated that prior to a diagnostic or treatment procedure, a diagnostic or treatment machine sends information to the transceiver identifying the patient for which the treatment was ordered. Upon receiving the identifying information, the transceiver processor compares the information to the patient identifying information stored in the transceiver memory. If the information received is identical to the information stored the transceiver does nothing or may send back a confirmation signal. However, if the information received and stored is different, transceiver 420 excites indicator device 428 thereby either audibly or visually indicating that the pending procedure should be halted.

Button 432 is also linked to the transceiver processor and can be depressed to manually cause transceiver 420 to transmit patient information. In addition, button 432 can be used in conjunction with display 424 to cause identifying information to either appear on or scroll across display 424. Moreover, button 432 could be an electronic lead which could be touched with an electronic probe attached to an HHD or the like to electronically transfer information from a bracelet memory.

In addition to having additional features, the manner in which transceiver 420 connects to bracelet 400 is different in this second embodiment. Instead of having alignment runners 136 (see FIG. 2), referring still to FIG. 11 and also to FIG. 12, bracelet 400 now forms two parallel tracks collectively referred to by numeral 404 which extend upwardly from identification surface 112 on opposite sides of memory section 120. Facing surfaces of tracks 404 form linear recesses collectively referred to by numeral 408 which traverse across bracelet width W. Recesses 408 define a distance D1 therebetween while distal ends of tracks 404 define a distance D2 which is slightly less than distance D1. An aperture 412 is formed by each track 404 which extends laterally and centrally through the track recess 408.

The outer shell of transceiver 420 is square having oppositely facing lateral surfaces collectively referred to by numeral 436 which define a transceiver dimension D3. Two lateral extensions collectively referred to by numeral 440 extend laterally from surfaces 436, a separate extension 440 extending from each of surfaces 436. The distal ends of extensions 440 define a dimension D4 which is greater than dimension D3. A spring loaded button 444 extends laterally and centrally from each lateral extension 440 (only one illustrated). Dimension D4 is essentially the same as dimension D1 while dimension D3 is essentially the same size as dimension D2. Thus, transceiver 420 fits within the space defined by tracks 404.

To secure transceiver 420 to bracelet 400, transceiver 420 is placed at either end of tracks 404 with extensions 440 aligned with recesses 408. Then transceiver 420 is forced along tracks 404 such that extensions 440 are received within recesses 408. Eventually, buttons 444 are forced outwardly through apertures 412 and secure transceiver 420 to bracelet 400. To remove transceiver 420 from bracelet 400, buttons 444 are depressed and transceiver 420 is slid out from between tracks 404.

One problem which might occur when attempting to interrogate a bracelet is that the bracelet might be positioned so that the bracelet transponder is not directly accessible. In this case, a person trying to identify the patient might have to reposition the bracelet, a procedure which should be avoided if possible. One other feature of the second embodiment which is different than the first is that this embodiment is designed so that it can transmit (and receive) infrared information from many secondary transmitters positioned at different bracelet surface points, thereby overcoming the position problem.

Figure 12:
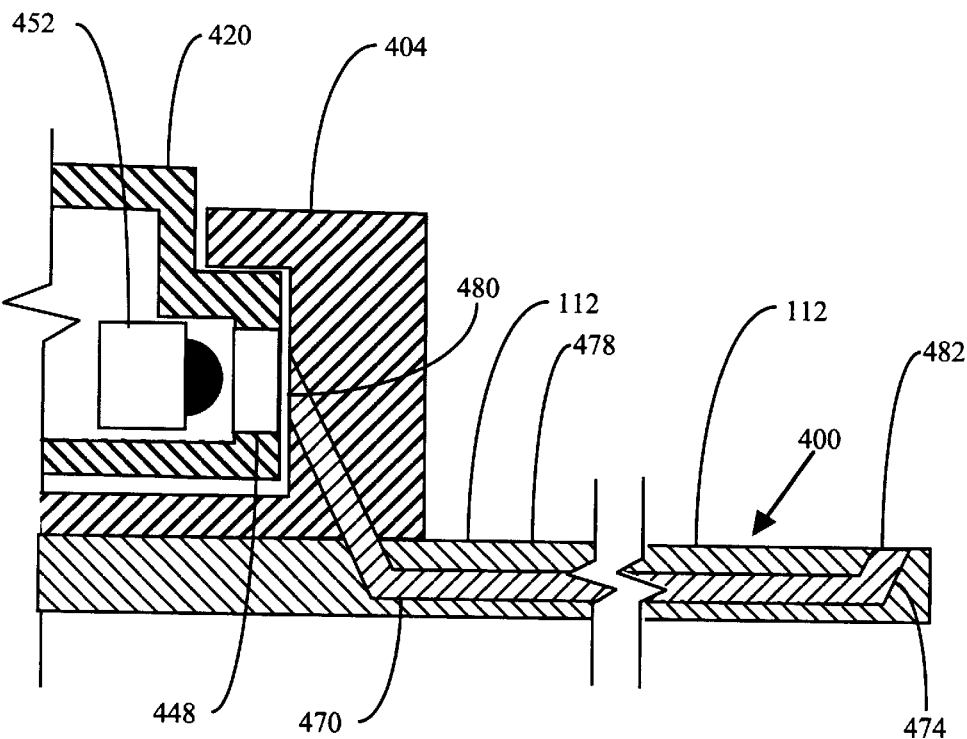
FIG. 12 is a cross sectional view of the bracelet of FIG. 11, albeit with the transceiver connected to the bracelet strap.

To this end, referring to FIGS. 11 and 12, a lateral transponder port 448 is formed by the transceiver shell in one of extensions 440 adjacent button 444. An infrared transponder 452 linked to the transceiver processor is positioned adjacent port 448 for transmitting and receiving infrared signals through port 448.

Bracelet 400, including one track 404, forms a channel 470. Channel 470 begins within recess 408, passes through track 404 and then through and along a length of the bracelet forming an outlet 474 which extends through identification surface 112. A fiber optic member 478 having proximal and distal ends 480 and 482 is positioned within channel 470, proximal end 480 within recess 408 and distal end 482 terminated at outlet 474. When transceiver 420 is secured to bracelet 400, port 448 is aligned with proximal end 480. Thus, light transmitted by transponder 452 is received by proximal end 480 and is again emitted through distal end 482. Similarly, light received by distal end 482 is emitted through proximal end 480 and is received by transponder 452.

Figure 13:
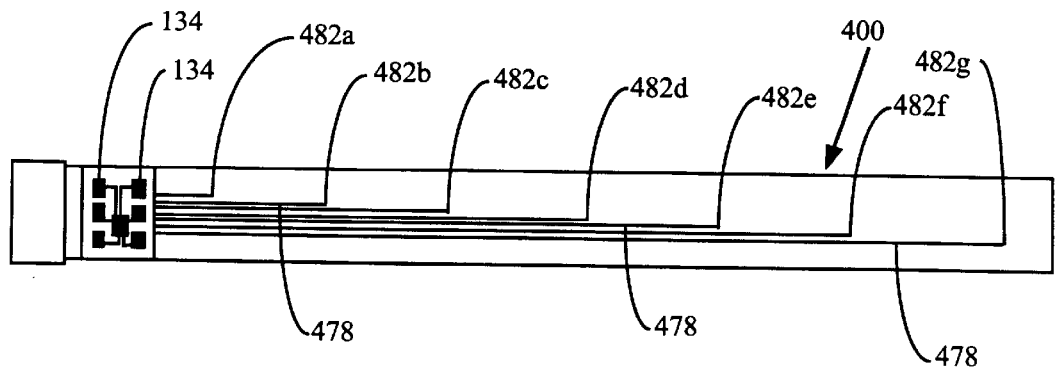
FIG. 13 is a top plan view of a preferred bracelet strap.

Referring also to FIG. 13, preferably, a plurality of fiber optic members 478 are provided within bracelet 400, each member distal end 482a, 482b, 482c, 482d, 482e, 482f and 482g terminating at a different position along the length of bracelet 400. It is contemplated that each member proximal end (not illustrated) would be adjacent port 448 so that a single transponder 452 could provide signals to and receive signals from each member distal end 482. In this embodiment bracelet 400 operates like a large antenna so that the bracelet is always in a position to receive and transmit information.

A variation on this embodiment might include an additional transponder linked directly to the transceiver which, when the transceiver is secured to the bracelet, wraps around the bracelet so that the second transponder is located on the opposite side of a patient's wrist from the main portion of the transponder. In this case, the transceiver could transmit and receive information on both sides of a patient's wrist.

Figure 14:
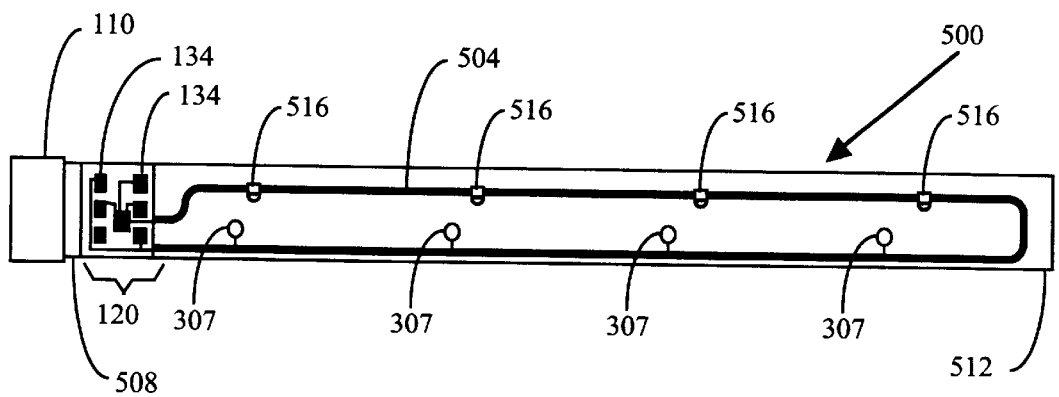
FIG. 14 is a view similar to FIG. 13, albeit of a third preferred embodiment of the inventive strap.

Referring also to FIG. 14, a third embodiment of the invention is illustrated. As transponders become less expensive, it is contemplated that it will become economically viable to provide a ring of discardable transponders on a bracelet 500. A conductive loop 504 having first and second loop ends and a midsection can be linked via contacts 134 to a transceiver processor (not illustrated). The loop 504 midsection traverses the length of bracelet 500 from a first end 508 to a second end 512. A plurality of transponders 516 are connected to loop 504. Signals to be transmitted are then provided to each transponder 516 for transmitting. Thus, this embodiment also solves the bracelet positioning problem by facilitating transmission and reception of signals from essentially all sides of bracelet 500.

In addition, this third embodiment is advantageous for other reasons. For example, loop 504 can be linked to contacts 134 such that when loop 504 is cut (e.g. to take bracelet 500 off), contacts 134 cannot impart or receive information from a transceiver processor. In this case, placement of memory section 120 is important. By placing memory section 120 next to clasp 110 at first end 508, loop 504 can traverse along essentially the entire length of bracelet 500 thereby making it nearly impossible to remove bracelet 500 without rendering the memory thereon unusable. Here, to remove bracelet 500 a person would have to cut through either memory section 120 or loop 504. An alternative where memory section 120 is centrally disposed along the bracelet length would be to provide a second loop (not illustrated) extending from memory section 120 in the direction opposite of loop 504 traversing the distance between memory section 120 and clasp 110.

Figure 15:
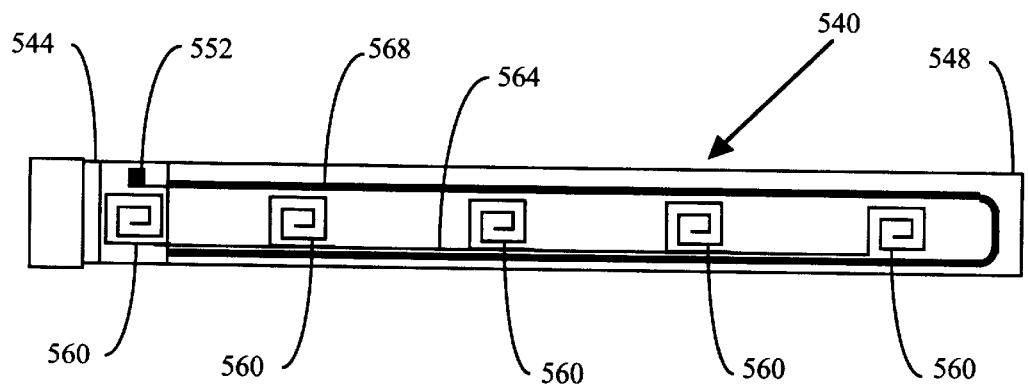
FIG. 15 is a view similar to FIG. 13, albeit of a fourth preferred embodiment of the inventive strap.

In addition to the embodiments described above, as transceiver circuitry becomes less expensive, it might become viable to have a transceiver built into a disposable bracelet. This is particularly true where only a small amount of patient identification information is required. For example, an HHD or a computer which interrogates a bracelet might be equipped with a patient data base for storing detailed patient information. In this case, the bracelet might only require a small amount of identification information such as a unique patient number. Once an HHD receives a patient number, the HHD can correlate the number with the patient's name and other information regarding the patient. In this case the transceiver processor would be extremely inexpensive and could be discardable.

Where an entire bracelet, including transceiver, is discardable, a particularly advantageous bracelet may be configured. Referring to FIG. 15, a fourth embodiment of an inventive bracelet 540 is illustrated. Bracelet 540 includes a strip of plastic or Kapton material having first and second ends 544, 548, respectively. A clasp 110 is linked to end 544 for connecting ends 544 and 548 together. A memory 552 is secured to bracelet 540 as are a plurality of rf transponder circuits collectively referred to by numeral 560. Memory 552 is linked to each of circuits 560 by a bus 564. A conductive loop 568 is also linked to each of circuits 560 to provide power thereto. To provide power to circuits 560, loop 568 is constructed such that, when placed within a specific signature magnetic field, a current is generated in loop 568 which powers circuits 560 and memory 552. When circuits 560 and memory 552 are powered, each circuit 560 transmits the abbreviated patient identification information stored in memory 552.

It is contemplated that an HHD can be equipped with a magnetic coupling device useable to generate the loop's signature magnetic field thereby imparting energy to circuits 560. When circuits 560 are energized, transmitted information is received by the HHD. Then, the HHD correlates the patient information with more detailed information which is presented to a health care worker for review.

This fourth embodiment has many advantages. In addition to imparting patient identification information without being touched, where loop 568 traverses the entire length of bracelet 540, bracelet 540 could not be removed without destroying loop 568 and thereby destroying the power source for circuits 560. Thus, once removed, bracelet 540 would not be able to identify a patient. In addition, no battery is required with this fourth embodiment.

In the alternative, the fourth embodiment might only include one circuit 560 or each circuit 560 might include its own loop 568.

One other advantage of this embodiment is that this embodiment can be configured in an extremely small and light-weight package and therefore is suitable for use with relatively weak facility occupants. For example, devices 540 configured in this manner would be advantageous for identifying infants or infirm patients for which a bulky clip-on transmitter device might be objectionable. In addition, identification devices of this type would not include removable components (e.g. a transmitter device) and would be completely sealed rendering these devices relatively safe for use with infants or small children.

In addition to the features described above, the present invention may also include a processor 240 which is programmed to indicate when transceiver 200 has been inadvertently removed from bracelet 104. To this end, processor 240 is programmed to, after transceiver 200 has been attached to bracelet 104, periodically identify if transceiver 200 is still fastened to bracelet 104. Where not fastened, processor 240 generates an alarm signal. In one embodiment the alarm signal is transmitted from the transceiver 200 to an external alarm indicator device.

Figure 16:
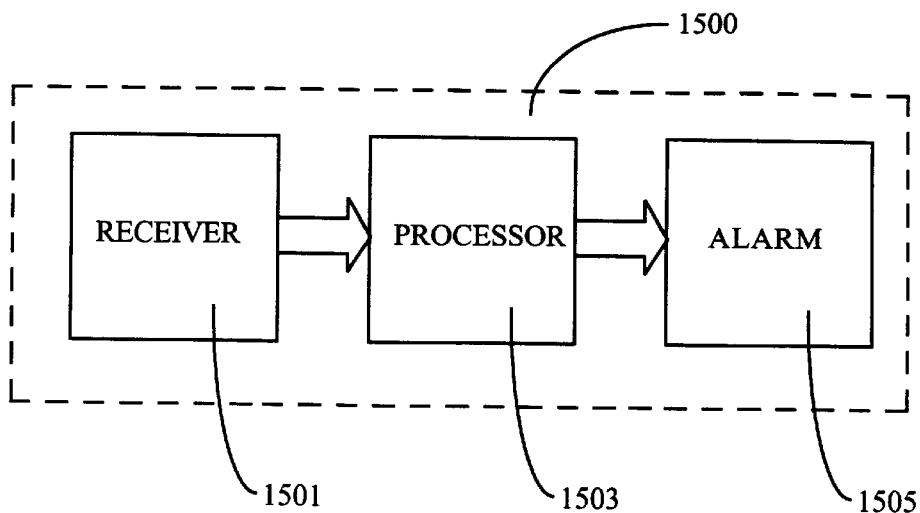
FIG. 16 is a block diagram of an external data collection device for use with the inventive apparatus.

Referring also to FIG. 16 an exemplary alarm indicator device 1500 includes a receiver 1501, a processor 1503 and an alarm 1505. Receiver 1501 receives the alarm signal and provides the signal to processor 1503 which in turn causes alarm 1505 to indicate that a transceiver has been inadvertently removed from a bracelet. The alarm 1505 may take any of several different forms but most preferably is an indicator on a computer screen or the like at an attending physician's work station. In this manner, although a transceiver has been removed and a physician has been notified, the patient is not startled.

Referring again to FIGS. 1, 3 and 4, in addition to the hardware described above, either one or both of an audible indicator 301 and a visual indicator 303 (e.g. LED) may be secured to circuit board and 248 and therethrough linked to processor 240. In this case, processor 240 (see FIG. 4) may be programmed to indicate via one or both of indicators 301 or 303 any of several different occurrences. For example, as above, when transceiver 200 is inadvertently removed from bracelet 104, processor 204 may indicate removal by LED 303 or speaker 301 or both.

In any embodiment where transceiver removal causes processor 240 to generate an alarm signal, it is contemplated that some mechanism would be provided for deactivating the processor 240 so that when a transceiver 200 is purposefully removed from a bracelet 104 the processor would not provide an alarm signal. An exemplary deactivation mechanism would be an HHD 300 (see FIG. 9) which can be used to provide a deactivation signal to the transceiver 200. In this case the processor 240 is programmed to recognize the deactivation signal and thereafter deactivate the alarm signal generating feature. Other deactivation mechanisms are contemplated.

As another example, indicators 301 and 303 can be used to indicate whenever processor 240 is in a specific or active state. To this end, a processor is in an active state when either receiving information, providing information or processing information and any combination of active states may be indicated via LEDs, audible sound, or the like. This feature enables a physician to determine which of a plurality of bracelets within a general area is receiving and transmitting data. For example, assuming a physician enters a room where first and second patients are located, each patient having an assembly 100 secured about a wrist. The physician intends to use an HHD 300 (see FIG. 9) to query the assembly 100 on the first patient's wrist and therefore approaches the first patient. Despite her intentions, the physician's HHD 300 may query the second patient's assembly 100 which would provide incorrect information to the HHD (i.e. the physician might believe the HHD information relevant to the first patient, not the second). With the audible/visual indicators, the physician can verify which assembly 100 is actually active (e.g. receiving or providing data) thereby avoiding a mix-up.

In addition, referring again to FIG. 14, in yet another embodiment of the invention, in addition to transponders 516 which are spaced along loop 500, a plurality of visual indicators (e.g. LEDs) collectively referred to by numeral 307 can be positioned along loop 500 for indicating processor active states. It is contemplated that the ring of indicators 307 would operate in a manner essentially identical to one of indicators 301 or 303 (see FIGS. 1 and 3) to indicate any of several different occurrences. In particular, processor 240 may be programmed to excite each of indicators 307 during a specific active state or during any of several different active states. This "ring" of LEDs enables a physician to identify an active processor despite bracelet position on a patient and is advantageous over an audible indicator for at least two reasons. First an audible indicator may startle a patient or wake a sleeping patient. This problem is avoided with the LED ring. Second, in a noisy environment, audible indication may be difficult to perceive whereas an excited LED is unmistakable.

Figure 17:
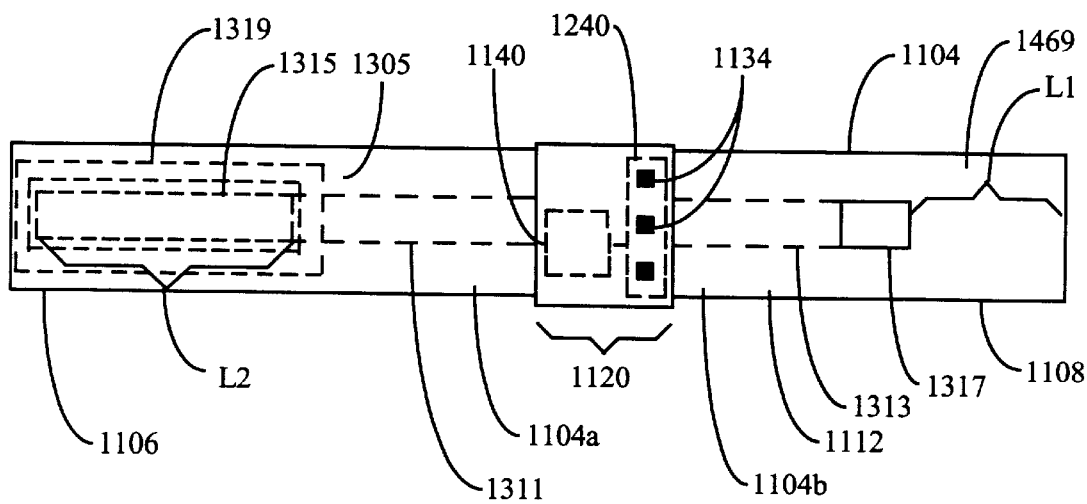
FIG. 17 is a top plan view of another preferred bracelet strap.
Figure 18:
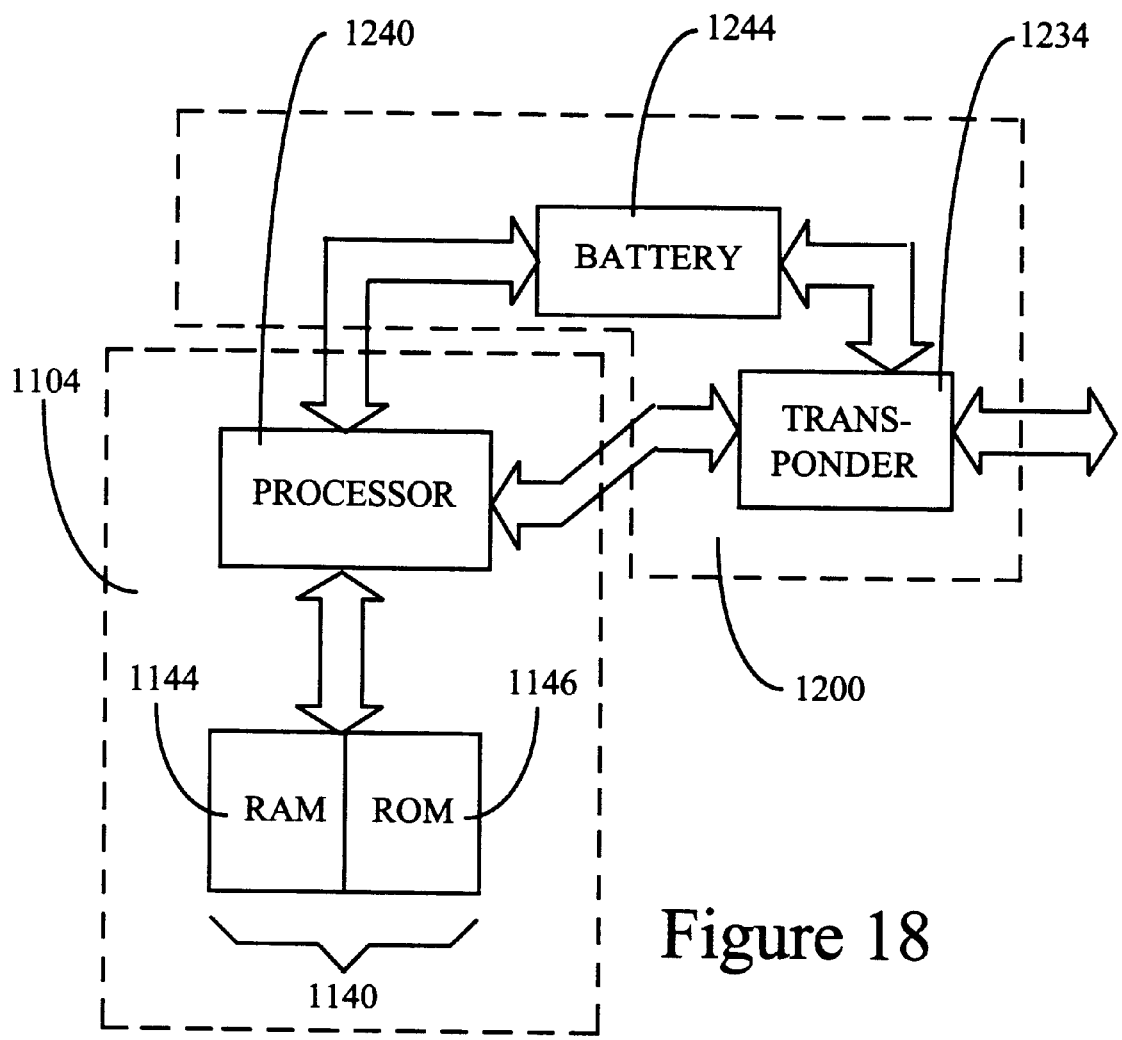
FIG. 18 is a block diagram of the electronics associated within an inventive bracelet strap.

Referring now to FIGS. 16, 17 and 18, a fifth embodiment of the invention is illustrated. This embodiment, like the others described above, includes both a bracelet 1104 and a transceiver 1200. Much of the construction and operation of this fifth embodiment is similar or identical to the construction and operation described above. For this reason only distinctions between the fifth embodiment and the embodiments above will be described here in detail. In FIGS. 17 through 20, elements which are similar to elements described with respect to the first embodiment above are identified by the same number proceeded by a A1.@ For example, while a processor is identified by numeral 240 above, the fifth embodiment processor is identified by numeral 1240 and so on.

With respect to noteworthy differences between the fifth embodiment and the other embodiments described above, referring to FIGS. 17, 18 and 19, bracelet 1104 includes first and second sections 1104a and 1104b, respectively, which extend in opposite directions form a fastening section 1120. The distal end of section 1104a is 1106 and the distal end of section 1104b is 1108. A memory device 1140 is secured to bracelet 1104 in section 1120 such that device 1140 cannot be removed without damaging bracelet 1104. Each of sections 1104a and 1104b has an external surface 1112 (viewable in FIG. 17) and an internal surface 1325 (see FIGS. 19 and 20) opposite surface 1112.

Figure 19:
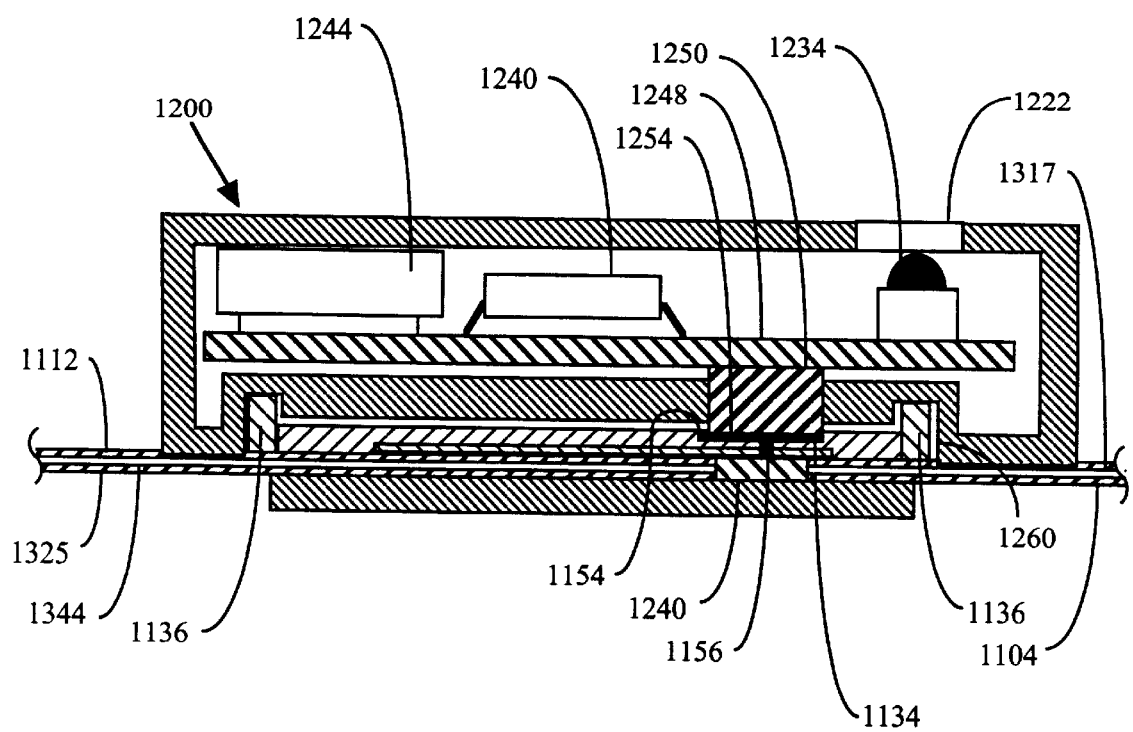
FIG. 19 is a view similar to the view illustrated in FIG. 4 albeit of another preferred embodiment.

While memory is currently relatively inexpensive, it has been recognized that processor hardware costs have been deteriorating appreciably recently and will soon reach the point where processor hardware may be disposable. Thus, it will be advantageous in some cases to provide disposable processor hardware on a disposable strap. Referring specifically to FIGS. 17, 18 and 19, to take advantage of the disposable nature of future processors in this fifth embodiment, instead of providing processor hardware in a reusable transceiver, processor 1240 is integrally secured to bracelet 1104 adjacent memory device 1140 and within section 1120 such that processor 1240 cannot be removed from bracelet 1104 without damaging the bracelet 1104. Processor 1240 is linked to memory device 1140. In this embodiment processor 1240 includes a plurality of processor contacts 1134 which extend up from proximal ends 1156 which link the processor to distal ends 1154. Distal ends 1154 contact transceiver contacts 1250 when transceiver 1200 is fastened to bracelet 1104.

Figure 20:
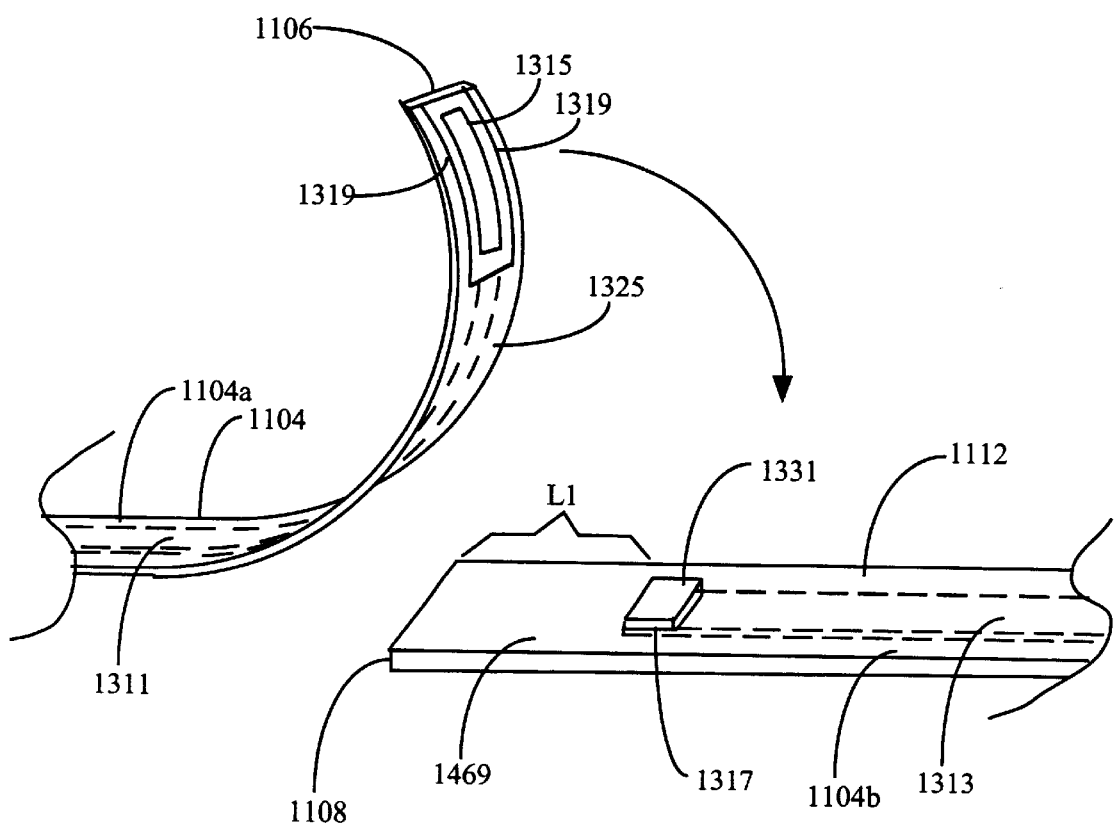
FIG. 20 is a perspective view of two strap ends according to one aspect of the present invention.

Referring to FIGS. 17, 19 and 20, first and second ribbon like conductive members 1311 and 1313 are encased in bracelet sections 1104a and 1104b, respectively. Proximal ends of each member 1311 and 1313 are linked to processor 1240. Section 1311 extends to end 1106 while section 1313 extends to within a distance L1 of end 1108. The portion L1 of section 1104b is referred to hereinafter as a flap 1469. A distal end 1315 of section 1311 having a length L2 is exposed through internal surface 1325 and a relatively smaller distal end 1317 of section 1313 is exposed through external surface 1112. An extending member 1331 extends up from portion 1317. Length L1 is slightly longer than length L2.

Referring still to FIGS. 19 and 20, glue strips collectively referred to by numeral 1319 surround end 1315 on internal surface 1325. To secure bracelet 1104 about a patient's wrist, bracelet 1104 is looped around the wrist such that internal surface 1325 faces the wrist and external surface 1112 faces outwardly. Then, member 1331 is aligned with end 1315 and surfaces 1325 and 1112 are pressed together so that the glue strips 1319 secure the ends together. When end 1315 and member 1331 are pressed together a short circuit forms therebetween and about the patient's wrist through processor 40.

It should be appreciated that by providing one relatively long exposed end 1315, one relatively short exposed member 1331 and flap 1469 adjacent short member 1331, loop length can be adjusted while still sealing the short circuit between members 1311 and 1313. This is because flap 1469 or some other portion of 5 bracelet 1104 covers member 1315 entirely despite positioning of member 1315 and end 1331. Thus, for example, on one hand where the distal end of member 1315 contacts end 1331 to provide a large loop, flap 1469 covers the remainder of member 1315. On the other hand, where the proximal end of member 1315 contacts end 1331, bracelet 1104 covers member 1315 to form a completely sealed and short circuited conductive member including members 1311 and 1313.

With the configuration as described above, after a loop and short circuit have been formed about a patient's wrist, processor 1240 can routinely check to determine if the loop (i.e. bracelet 1104) has been cut. If the loop has been cut rendering the bracelet unsecured, the short circuit through members 1311 and 1313 is broken. To indicate an unsecured bracelet, processor 1240 can be equipped to perform any of several different indicating functions. For example, if transceiver 1200 is fastened to bracelet 1104, processor 1240 may be programmed to cause indicators 1301 or 1303 to indicate a cut. In the alternative, processor 1240 may cause transceiver 1200 to send an alarm signal to an external alarm device (see FIG. 16) to indicate an unsecured bracelet.

According to yet another aspect of the invention any of the embodiments above can be used to facilitate data tracking and gathering where a patient is transferred from one medical facility to another. For example, a primary physician may want to track a patient's medical records as a patient is moves from a hospital into a nursing home for extended care. To this end, while the patient is in the hospital it is contemplated that a bracelet of the above kind is secured in a loop about the patient's wrist. With the bracelet secured a transceiver is fastened to the bracelet. The transceiver and bracelet are used together while the patient remains in the hospital. Prior to leaving the hospital and entering a nursing home, the physician uses her HHD (see 300 in FIG. 9) to transmit an Internet network address corresponding to the physician to the transceiver. The processor receives the address and stores the address in the memory device 140 or 1140 for use at the nursing home to deliver reports back to the primary physician. Before the patient leaves the hospital, the transceiver is removed and therefore the bracelet is rendered dormant, although the bracelet still maintains the patient information, including the physician's Internet address in the memory device.

When the patient arrives at the nursing home, a second transceiver identical in design to the first transceiver is fastened to the bracelet to perform all of the functions indicated above. In addition, the second transceiver is used to transmit the primary physician's Internet address to an external device and into the nursing home's Internet system where the address is stored. The external device would include a receiver, a processor and a memory storage device for storing the received data. Thereafter, any time data is added to the nursing home's computer system which corresponds to the patient, the information is also automatically delivered to the primary physician's network address so that the primary physician can track patient care. This type of automated system cuts down paperwork and the like required to apprize all persons involved in patient care and also cuts down on information errors.

Figure 23:
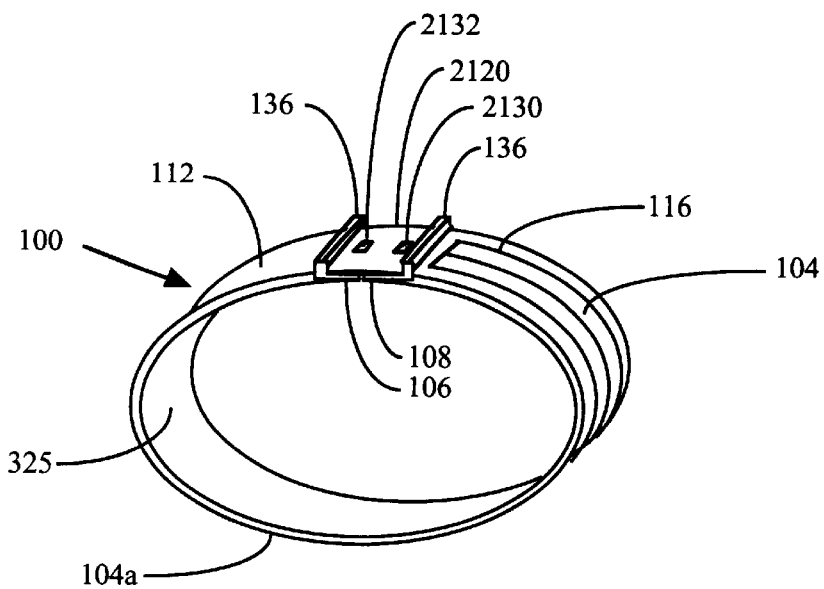
FIG. 23 is a perspective view of another embodiment of the bracelet strap.
Figure 24:
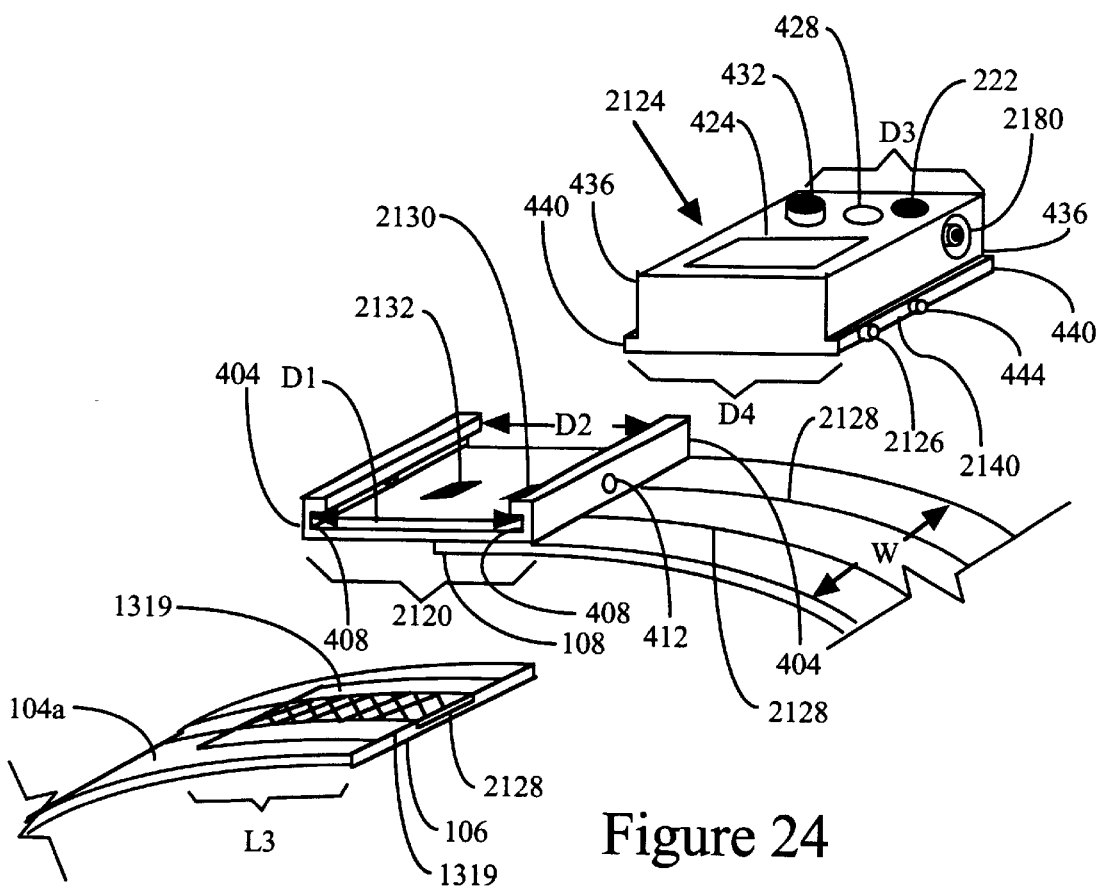
FIG. 24 is a perspective view of a sixth embodiment of an inventive identification bracelet with a transceiver disconnected from the bracelet strap of FIG. 23.
Figure 25:
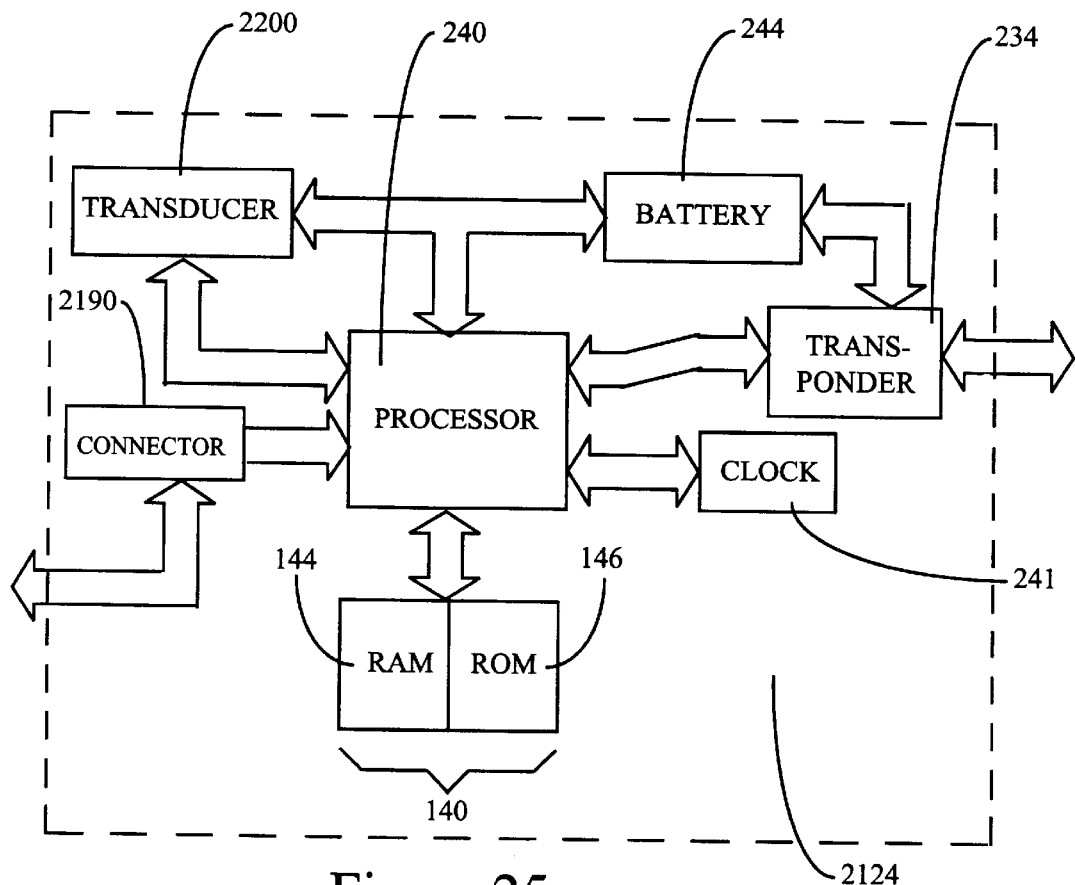
FIG. 25 is a block diagram of the electronics associated with the sixth embodiment of the present invention.

Referring now to FIGS. 23, 24, and 25 a sixth embodiment of the invention is illustrated. This embodiment, like the others above, includes both a bracelet 104 and a transceiver 2124. Much of the construction and operation of the sixth embodiment is similar or identical to the second embodiment and others above in construction and operation. For this reason only the distinctions between the sixth embodiment and the embodiments above will be described here in detail. In FIGS. 23, 24, and 25 elements that are similar to elements described in the previous embodiments use similar numbers. For example a processor identified by the numeral 240 is identified by the same numeral in the sixth embodiment.

With respect to noteworthy differences between the sixth embodiment and the other embodiments described above, referring to FIGS. 23, 24 and 25, bracelet 104 includes section 104a which extends in the opposite direction from a fastening section 2120. Section 104a has a distal end 106 and an opposing end 108 which is joined to the fastening section 2120. In this embodiment there is no memory chip attached to bracelet 104. Bracelet 104 has an external surface 112 (viewable in FIG. 23) and an internal surface 325 (see FIGS. 23) opposite surface 112.

In this embodiment memory chip 140 used to store identifying information is contained in transceiver 2124 (see FIG. 25). While memory is currently relatively inexpensive, there are some extremely cost-sensitive applications for identifying a patient (e.g., identification within a doctors office). Thus, it will be advantageous in some cases to provide a disposable strap, without memory, and a reusable transceiver with memory.

Referring specifically to FIGS. 25 instead of providing memory in a disposable strap, memory 140 is an integral part of transceiver 2124 such that transceiver 2124 can be removed from bracelet 104 either without damage to bracelet 104 or in other situations in which it is desirable that the removal of transceiver 2124 must be done in a tamper evident manner.

Referring to FIG. 24, glue strips collectively referred to by numeral 1319 are placed at distal end 106 on external surface 112. To secure bracelet 104 about a patient's wrist, bracelet 104 is looped around the wrist such that external surface 112 faces outwardly. Then, fastening section 2120 is aligned with end 106 and surfaces 112 and 325 are pressed together so that the glue strips 1319 secure distal end 106 to the underside of fastening section 2120. Other methods of securing the distal end 106 of section 104a to the fastener section 2120 of the bracelet are contemplated and well know in the prior art.

Transceiver 2124 can include a display 424, an indicator device 428 and a button 432. It is contemplated that display 424 might be an LCD linked to a transponder processor (similar to FIG. 10) for visually imparting patient identifying information. When display 424 is used to display patient identification information, bracelet 104 need not have any identifying text written on it.

Operation of the sixth embodiment is similar to that of the second embodiment, however, there are several differences. First, memory chip 140 in transceiver 2124 can be programmed with patient identification information by signals sent from HHD 300 (also referred to herein as an enabling component or device) or a separate computer equipped with a compatible transponder 308. The memory chip 140 can be programmed either before or after transceiver 2124 has been attached to fastener section 2120.

Second, transceiver 2124 also has attachment sensor 2126 that detects when transceiver 2124 has been attached to fastening section 2120 via the engagement of the first and second latch derius, such as tracks 404 and extensions 440. Sensor 2126 is shown as an electrical button that, when lateral extension 440 is placed in recess 408 of the fastening section, is depressed forming a short circuit that is monitored by processor 240. In this manner processor 240 is able to determine when the transceiver has been placed in fastening section 2120 and when it is removed. Sensor 2126 can be in the form of a light emitter-detector where recess 408 includes a light reflector, electrical contacts, or a magnetic sensor where the recess includes a magnet. Other sensors are contemplated. For example, the sensor 2126 can include a first sensor coupled to the transceiver and a second sensor coupled to the bracelet or any other base member to which the transceiver is attached.

Third, once memory chip 140 has been programmed and processor 240 has determined (via sensor 2126) that transceiver 2124 has been attached to bracelet 104, the transceiver 2124 provides patient identification information to HHD 300 or other computer devices with compatible transponders 308. The transceiver 2124 can also receive information for storage in memory chip 140 from HHD 300. However, when transceiver 2124 is removed from fastening section 2120 by pressing buttons 444 through apertures 412, sensor 2126 detects the removal and processor 240 is notified of the removal by the presence of an open circuit. When the transceiver is removed processor 240 can perform one of several "security" functions.

One security function is for processor 240 to erase the contents of memory chip 140, thereby preventing patient identification information for one patient being accidentally provided when transceiver 2124 is attached to another strap 104 corresponding to another patient. Another security function is for processor 240 to inhibit transmission of patient identification information to HHD 300 and inhibit reception of information to be stored in memory chip 140 from HHD 300. However, in this case transceiver 240 will transfer the contents of memory chip 140 when transceiver 2124 receives a special coded message from a HHD used to retrieve the contents of the memory chip prior to reusing transceiver 2124 for another patient. Once again information in transceiver 2124 cannot be associated with the wrong patient. Another security function is for processor 240 to clear or erase memory chip 140, but only when transceiver 2124 is attached to another strap 104. When transceiver 2124 includes display 424, another function is for processor 240 to no longer display patient identification information when the transceiver is removed from the bracelet.

Another security function is to record in memory 140 the time from clock 241 when transceiver 2124 is removed from bracelet 104. Yet another function is to disable access to the memory until a special code or event occurs, at which point the disabled memory can be re-enabled.

Another function is for transceiver 2124 to issue an alarm signal, as previously described, indicating that it was removed from the bracelet 104. The alarm signal can be inhibited by a special code being sent to transceiver 2124 from HHD 300.

In any of the aforementioned cases when some system component is disabled or an alarm is generated, the security function may further include monitoring for an enabling component on the transceiver for an access code and when the code is received, either re-enabling the disabled component or ending the alarm. Referring to FIG. 25, where the security function is to disable memory 140, a transponder 234 including a receiver may be the enabling component which may be equipped to receive an access code from an HHD (see 300 in FIG. 9). In the alternative, where the security function includes disabling transponder 234 (i.e., disabling a receiver/transmitter), a separate enabling component 233 such as a mechanical button for receiving a "morse-like" code may be provided. Processor 240 performs the access code monitoring step.

Bracelet 104 can also include a conductive member 2128 encased in bracelet 104 similar to the conductive members 1311 and 1313 shown in FIGS. 17 and 20. Conductive member 2128 is attached to electrical contact 2130 where bracelet 104 mates with fastening section 2120. The portion L3 of section 1104a is referred to hereinafter as a flap 1469. The distal end 106 of section 1104a has member 2128 exposed through external surface 112. When bracelet is looped around a patient's wrist and secured as previously described, conductive member 2128 is placed in electrical contact with contact 2132 of fastener section 2120. Accordingly, transceiver 2124 also has electrical contacts 2140 on its underside to mate with contacts 2130 and 2132 when attached to fastener section 2120, similar to contacts 250 and 1250, described in prior embodiments. Processor 240 can now use contacts 2140 as sensor 2126 to determine that transceiver is attached to bracelet 104 as previously described. Now if bracelet 104 is removed from the patient processor 240 can perform any of the functions mentioned above regarding erasing memory chip 140, no longer transferring memory contents, no longer displaying identification information, and presenting an alarm signal.

Conductive member 2128 can also be used to provide signals to additional transponders 504 spaced around bracelet 104 similar to those shown in FIG. 14 and described in the second embodiment. Alternatively, conductive member 2128 can be used to provide signals to one or more additional indicator devices 428 spaced around bracelet 104. When transceiver 2124 is in communication with HHD 300, processor 240 can use indicator devices 428 to indicate to the user of the HHD the patient the user is in communication with without having to orient transceiver 2124 to a viewable or hearing position and thereby reduce manipulations to the patient's wrist to orient the transceiver.

Figure 26:
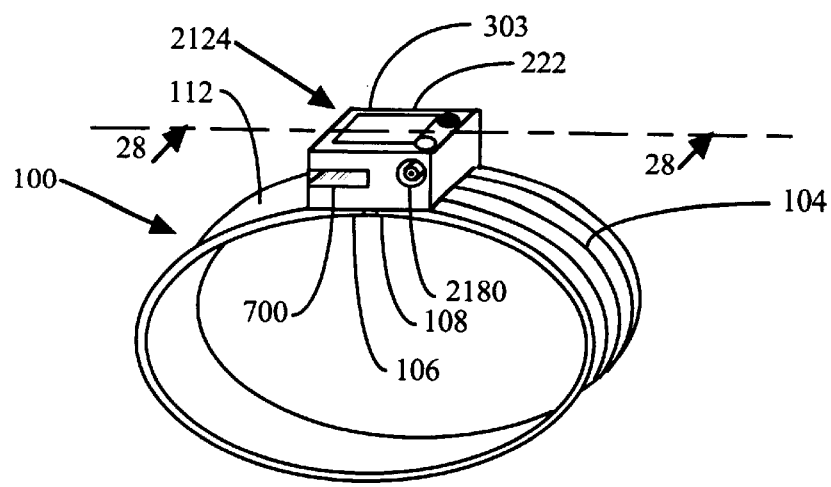
FIG. 26 is a perspective view of a seventh embodiment of an inventive bracelet including an attached transceiver having a data card reader slot.
Figure 27:
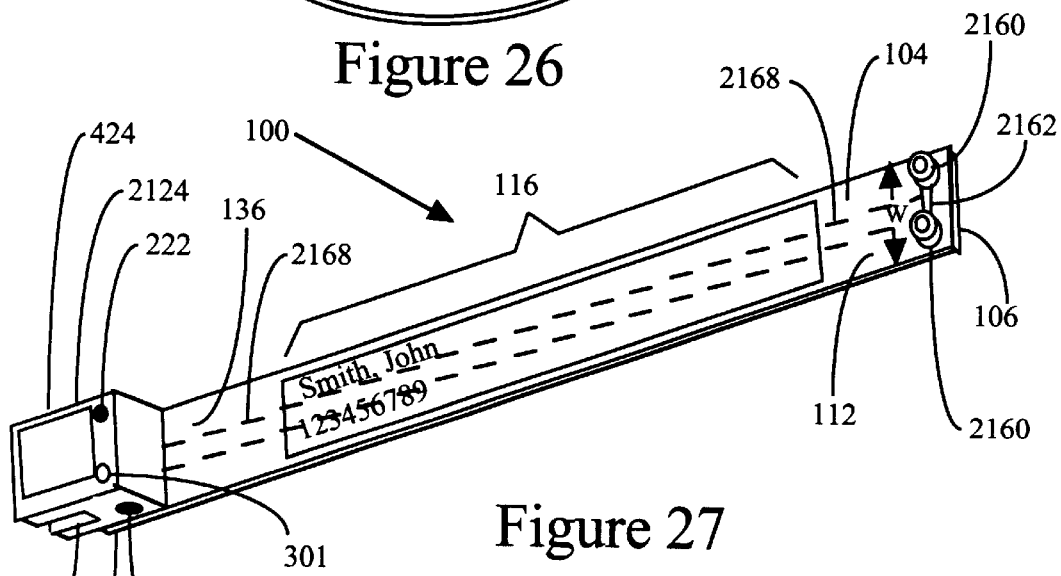
FIG. 27 is a perspective view of the bracelet of FIG. 26, albeit in a flat configuration prior to forming a loop.
Figure 28:
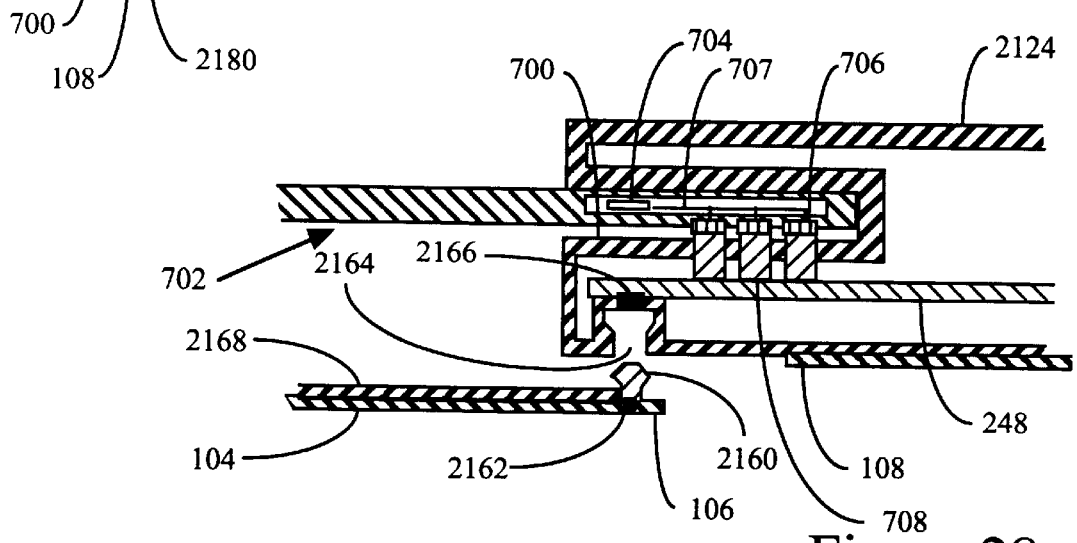
FIG. 28 is a cross sectional view taken along the line 28—28 of FIG. 26, albeit with the bracelet strap not completely formed in a closed loop.

FIGS. 26, 27, and 28 illustrate a seventh embodiment of the invention. This embodiment unlike the others above has the transceiver as an integral part of bracelet 104, and the transceiver or information apparatus, is capable of receiving information from an object data device, such as a data card. However, much of the operation of seventh embodiment is similar to the operation of the sixth embodiment, and for this reason, only the distinctions between the seventh and sixth embodiment will be described in detail.

As shown in FIG. 27 transceiver 2124 is placed at one end of bracelet 104 and at the distal end 106 of the bracelet are snaps 2160 and electrical conductor 2162 connecting the two snaps together. To secure bracelet 104 about a patient's wrist, bracelet 104 is looped around the wrist such that exterior surface 112 faces outwardly. Then snaps 2160 at the distal end 106 are aligned with matching snap holes 2164, the snaps are then pressed into the holes securing bracelet 104 to the wrist. When the snaps 2160 are pressed into holes 2164 the snaps are placed in electrical contact with contacts 2166 attached to circuit board 248 of transceiver 2124. Processor 240 monitors for the presence of the short circuit between the contacts 2166 caused by snaps 2160 and conductor 2162, indicating that the bracelet is attached to a patient's wrist.

As previously described for the sixth embodiment, when bracelet 104 is attached to the patient, the patient information in memory chip 140 can be sent to HHD 300 and other information can be received from HHD 300 for storage in the memory chip.

If bracelet 104 is removed from the patient processor 240 can perform any of the security functions mentioned above regarding erasing memory chip 140, inhibiting transfer of memory chip contents, no longer displaying identification information, recording of the time removal, and presenting an alarm signal. As an alternative, processor 240 can be linked to conductive member 2168 which is electrically connected to processor 240 in transceiver 2124 and to snaps 2160. In this case processor 240 monitors for a short circuit between one end of conductive member 2168 around bracelet 104 and thorough one or more of snaps 2160 and contacts 2166. Conductor 2168 ensures that processor 240 is able to continuously monitor that the bracelet is secured to the patient and that even if the bracelet is cut the functions previously described will be performed. This embodiment is advantageous as it allows for a convenient and reusable bracelet to be used to identify patients with identification information, yet if the bracelet is moved from a first patient and secured to a second patient there is no chance of information related to the first patient being associated with the second patient.

Conductive member 2168 can also be used to provide signals to additional transponders 504 spaced around bracelet 104 similar to those shown in FIG. 14 and described in the second embodiment.

As best shown in FIGS. 26, 27 and 28, the transceiver 2124 includes a data reader 699 having pass-through slot 700 extending transversely through the transceiver 2124. The slot 700 is sized to receive an edge portion of an object data device, such as a data card 702 having a memory device 704 linked to one of more readable or interface segments such as conductive contacts 706 by a suitable conductor 707. The slot 700 is also sized so that the data card 702 may be disposed within and passed through the slot 700 such that the contacts 706 physically contact terminals 708 linked to the processor 240 of the transceiver 2124. Data stored in the card memory device 704 can be transferred through the terminals 708 to the memory chip 140 of the transceiver 2124. The reverse process can also be conducted such that data stored in transceiver memory chip 140 can be transferred to the card memory device 704. However, it is preferably that before data is transferred to the card memory device 704 a comparison be made between a portion of the basic information in memory chip 140 and the card memory device 704, if there is a match then the data can be transferred otherwise an alarm can be presented indicating that a card for a different patient has been presented.

Preferably the data card 702 is a "Smart Card" type memory device having read/write data storage capabilities, as known in the art. However, the data card may also be any other suitable object data storage device, such as card having a bar code or magnetic strip, like a credit card. Moreover, the memory is preferably read/write memory, however, read only memory cards could also be used with the present invention.

Also, once data is transferred from a data card 702 having data pertaining to the object or person to which the transceiver 2124 is attached, preferably, the transceiver 2124 will not transfer data to or from a data card pertaining to an other object or person unless a special code is supplied from a control card or other external device, such as HDD 300.

Figure 29:
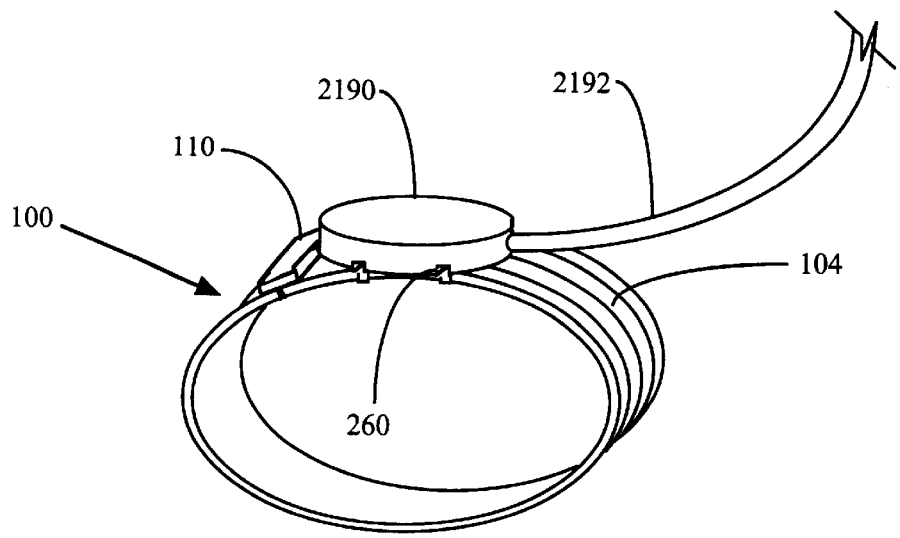
FIG. 29 is a perspective view of an eighth embodiment of an inventive bracelet of the present invention having a connector attached to it in communication with another device.

In an eighth embodiment of the present invention, shown in FIG. 29, memory (not shown) affixed to the bracelet 104 is coupled to external identification electronics (not shown) via a cable 2192 attached to the bracelet 104 by connector 2190 at clasp 110. In this embodiment, identification and other such data is transferred to and from the memory on the bracelet 104 via the cable 2192 to a control computer, measurement devices or other such electronic equipment.

Figure 30:
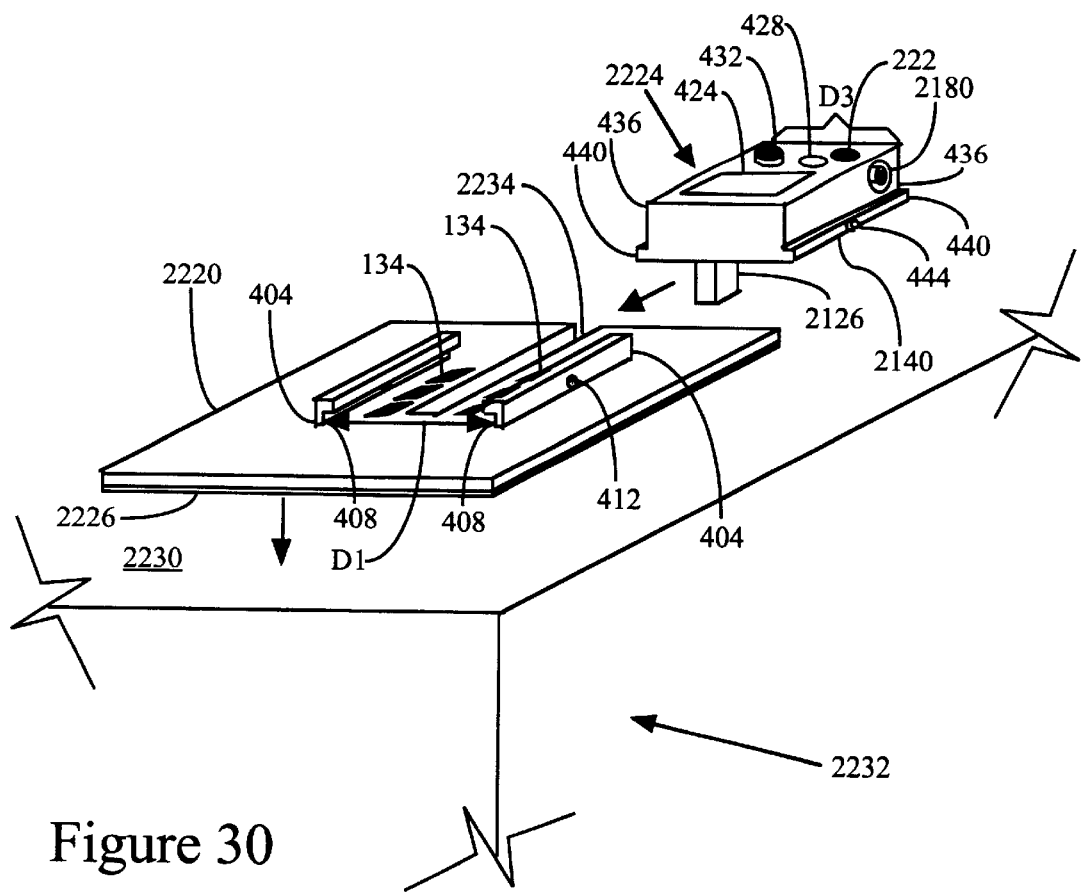
FIG. 30 is a perspective view of an ninth embodiment of a transceiver and mating fastener section similar to that of the first and second embodiments.

In a ninth embodiment of the present invention, shown in FIG. 30, the bracelet 104 is now replaced by fastener section 2220. Fastener section 2220 and transceiver 2224 are similar to fastener section 120 and transceiver 420 of the second embodiment of the present invention shown in FIG. 11. In this example, fastener section 2220 is shown as an independent platform with contacts 134 attached to a memory chip. Parallel tracks 404 with recesses 408 allow transceiver 2224 to be slid onto and secured to fastener section 2220. As before, button 440 is depressed allowing lateral extensions 440 to pass into recesses 408. When button 444 is aligned with aperture 412, button 444 extends outwardly holding transceiver 2224 to the fastener section. When so aligned contacts 250 (not shown in FIG. 30) of the transceiver make electrical contact with contacts 134, allowing processor 240 to be in communication with memory chip 140.

Transceiver 2224 can use connector 2180 to receive measurements related to object 2232 from other parameter measuring devices for storage in memory chip 140 and transceiver can include transducers to directly measure and store parameter measurements.

Fastener section 2220 has an adhesive layer 2226 on its lower side so that it can be conveniently affixed to surface 2230 of object 2232. Other forms of affixing are contemplated as described above.

In a variation of the ninth embodiment, the fastener section 2220 does not have contacts or a memory chip. Instead memory chip 140 is part of transceiver 2220 as described in the sixth embodiment.

Figure 31:
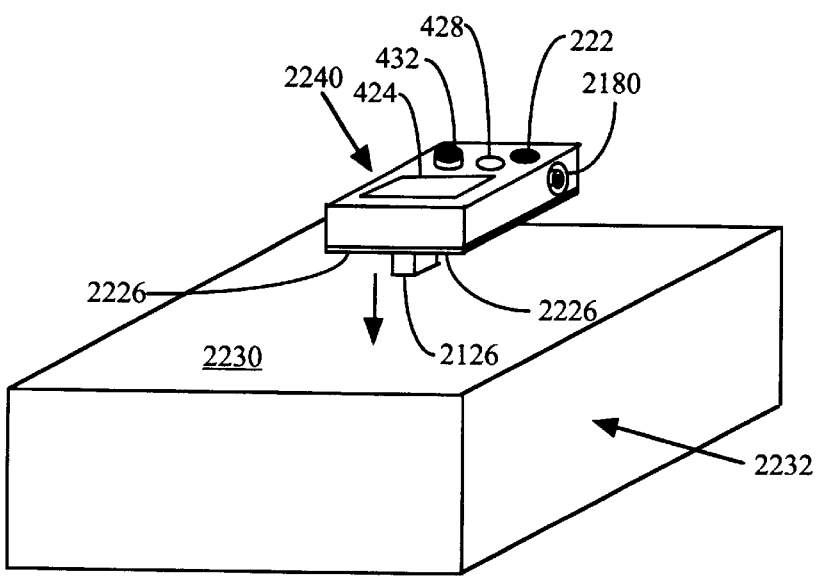
FIG. 31 is a perspective view of a tenth embodiment of a transceiver mounted to an adhesive base.

A tenth embodiment of the present invention is shown in FIG. 31. In this embodiment transceiver 2240 is directly affixed to surface 2230 using adhesive layer 2226. Transceiver is similar to transceiver 2124 of the seventh embodiment and includes memory chip 140. Transceiver 2240 can use connector 2180 to receive measurements related to object 2232 from other parameter measuring devices for storage in memory chip 140 and transceiver 2240 can include transducers to directly measure and store parameter measurements. Preferably, these stored parameters will include the time of their measurement which may be provided by the connected transducer or by a clock that is part of processor 240 or in communication with processor 240.

Transceiver 2240 uses attachment sensor 2126 to determine that is continues to be affixed to surface 2230. As long as transceiver 2240 continues to be affixed to surface 2230 it can display and transfer identification information related to object 2232. When removed processor 240 can perform any of the functions mentioned above regarding erasing memory chip 140, no longer transferring memory chip contents, no longer displaying identification information, and presenting an alarm signal.

Figures 32, 33:
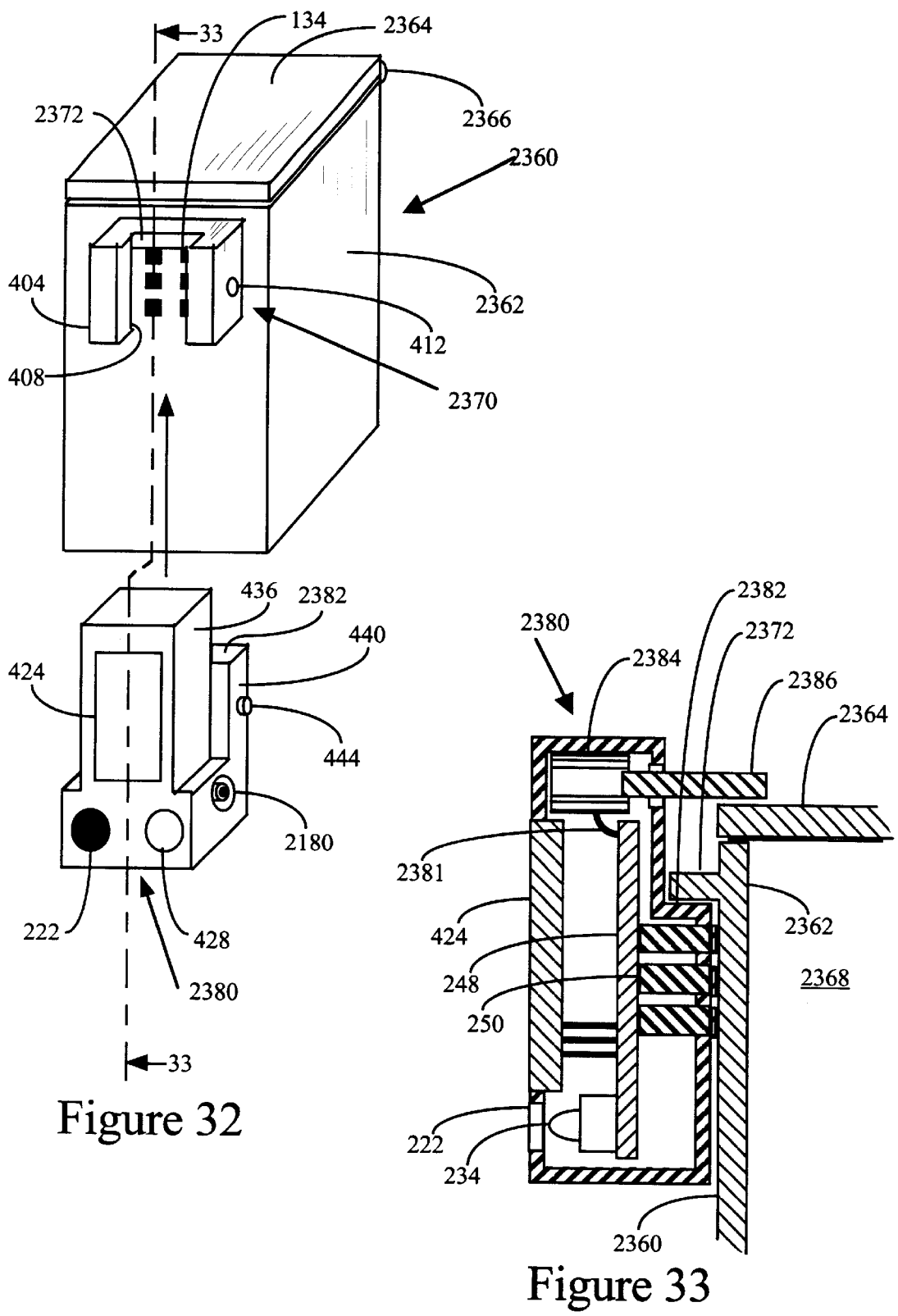
FIG. 32 is a perspective view of an eleventh embodiment of the present invention similar to the first and second embodiments of a transceiver secured to a container.
FIG. 33 is a cross section view taken along the line 32—32 of FIG. 32, albeit illustrating the transceiver of FIG. 32 secured to the container of FIG. 32.

An eleventh embodiment of the present invention is shown in FIGS. 32 and 33. In this embodiment, primary apparatus components include the transceiver 2324 and a container vessel 2360. The container 2360 is comprised of base 2362 and top referred to also as a closure member 2364 (shown in the closed position), which is attached to the base by hinge 2366, together defining compartment 2368. Fastener section 2370 is an integral part of container base 2362. Fastener section 2370 includes contact 134 and memory chip 140 (not shown) and parallel tracks 404 with recesses 408. Unlike the second embodiment fastener section 2370, recesses 408 do not extend completely through tracks 404, as they are blocked by wall 2372. In this case transceiver 2324 is similar to transceiver 420 of the second embodiment. Transceiver is designed to mate with fastener section 2370 in only one orientation; by engaging lateral extensions 440 into recesses 408, buttons 444 being depressed allowing lateral extensions 440 to continue to pass into recesses 408, and sliding transceiver 2380 up until head wall 2382 reaches wall 2372. At this point buttons 444 are aligned with apertures 412, the buttons extend outwardly holding transceiver 2224 to the fastener section. When so aligned contacts 250 (see FIG. 33) of the transceiver make electrical contact with contacts 134 allowing processor 240 to be in communication with memory chip 140. While the cap is shown using a living hinge, other cap methods are contemplated such as screw on or press-fit on caps.

Memory chip 140 may then be programmed with identification information related to the contents of container 2360 (for example information relating to a medication placed in container) using transceiver 2380 to receive the identification information including name, identification number, etc., from HHD 300 or the memory chip may have been previously programmed with such identification information. The basic identification information may identify to whom the contents of the container are to be given. When transceiver 2380 is attached to fastener section 2370 and the memory has been programmed with identification information, processor 240 of transceiver 2380 uses electrical connector 2381 to activate solenoid 2384, causing the solenoid 2384 to extend to position 2386. In the extended position solenoid 2384 prevents top 2364 from being opened and transceiver 2380 cannot be removed from the fastener section without damaging either container 2360 or transceiver 2380.

Transceiver 2380 operates as do transceivers 200 or 420 described above, providing identification information to HHD 300 or to any of the transceivers 200, 420, and 2124 previously described.

To open top 2364, transceiver 2380 must receive a special code from HHD 300 that is compared to a portion of identification information in memory chip 140 of fastener section 2370. When the code matches a portion of the identification information, processor 240 of transceiver 2380 activates solenoid 2384 moving it to a retracted position, allowing top 2364 to be opened and when desired, transceiver 2380 to be removed from fastener section 2370. The special code can be patient identification information for a patient to whom the contents of container 2360 is to be given, the code coming from a bracelet 104. Alternately transceiver 2364 can retract the solenoid at specified times, in response to a measured parameter received or measured by transceiver 2364, or as a result of specific events. The solenoid operation data or code can be supplied by an external device or stored in the memory.

In a variation of the eleventh embodiment of the present invention, the fastener section 2370 does not include memory chip 140 and contacts 134. Instead memory chip 140 is part of transceiver 280. In this embodiment, processor 240 of transceiver 2380 can extend solenoid to extended position 2386 when transceiver 2380 is attached to container 2360 and has received identification information from HHD 300.

Processor 240 monitors when transceiver 2380 is removed from fastener section 2370 or when the fastener section is removed from surface 2230 via any of the sensing methods described above. When transceiver 2380 is removed, processor 240 can perform any of the security functions discussed previously.

D. Operation of Invention to Label Information

In previous embodiments of the invention the transceivers can be used to receive information about the patient from HHD 300 or other devices. To ensure that the information being received is related to the patient the information should be labeled with patient identification information so processor 240 can compare this information with that previously stored in memory chip 140. If there is a match the data is stored in memory, if there is no match the data is not stored and an alarm signal can be generated.

While this method of verifying data is useful, there may be a number of medical devices used on a patient that do not have any provision for identifying the patient. These devices can be used to monitor parameters regarding the patient, such as blood pressure, heart rate, or room temperature. In this case transceivers 200, 420, and 2124 (see FIGS. 24, 25, and, 27) can use connector 2180 that allows a medical device associated with the patient to send measurements to processor 240 for storage in memory chip 140. Once stored in memory chip 140, the measurements will be associated or labeled with the patient identification information previously stored.

Alternately, for embodiments where a memory chip 140 is part of a bracelet (see embodiments 1 through 5) the transceiver can be replaced by a similarly shaped connector 2190 (see FIG. 29). The connector can be attached by cable 2192 to a medical device to monitor a parameter regarding the patient. The medical device sends measurements to the memory chip for storage. The measurements are labeled with the patient identification information previously programmed in the memory chip. The memory contents can be read by removing the connector and replacing it with a transceiver 200, 420, or 2124 to transfer the measurements to HHD 300 or the HHD can be equipped with another connector to directly read the memory chip using the electrical contacts 134 or 1134. The time of each measurement may be provided by the medical device or clock 241 in communication with processor 240 and is recorded with the measurement.

Alternately, in any of the embodiments a transceiver can be equipped with transducer 2200 (see FIG. 25) to measure a parameter regarding the patient. In this case the transceiver can record the measurements in the memory chip 140, again labeling the measurements with the patient identification information. As described in the third embodiment, removal of the bracelet 104 by cutting a conductive loop or member can result in the memory chip 140 no longer being able to receive information for storage.

E. Using a Personal Area Network for Communication

Personal area networks (PAN) are well known and therefore will not be explained here in detail. For background regarding capabilities and general understanding of an exemplary PAN, see U.S. Pat. No. 5,914,701 which issued in 1997. A personal area network can use two devices that are in proximity with a person, but not necessarily touching the person. They can communicate with each other using a local near-field electrostatic coupling. Information is transferred by modulating an electrostatic coupling of current into the body (capacitive coupling). A sufficiently low carrier frequency (e.g. 300 kHz) can be used to minimize the propagation of the communications signal energy beyond the body.

Many uses have been proposed for PANs. For example, it has been contemplated that a PAN can be used to exchange information between a cellular telephone in a users pocket to a personal digital assistant in another pocket. It is contemplated that the above embodiments of the transceiver can use PAN as a means of receiving information from or sending information to an HHD 300. Further, by using a PAN many medical devices that use electrodes or probes placed on a patient can automatically receive the patient identification information, passing the carrier frequency and modulated signals through the electrodes or probes and through the device's front end amplifiers or filters to a demodulator. After being demodulated the device will have received the patient identification information. As long as the electrodes or probes remain on or very near the patient the medical device will associate any measurements or data recordings with the patient identification information. When the electrode or probe is no longer near the patient the medical device will no longer receive patient identification information and may discontinue collecting measurements or data recordings. An instrument can only receive patent identification information from the patient the probe or electrode is in close proximity to and therefore will not collect such information from any other patient. Similarly, as long as the electrode or probe is near the patient the medical device can send information through its front-end amplifiers for near-field electrostatic coupling to the patient's body to be received by a transceiver.

It should be understood that the apparatuses described above are only exemplary and do not limit the scope of the invention, and that various modifications could be made by those skilled in the art that would fall under the scope of the invention. For example, in some embodiments two fasteners are described above for connecting a transceiver to a bracelet, however, clearly other fasteners could be used to make this connection. In addition, while the present invention is described using infrared transponders, other types of transponders (e.g. rf transponders) could be used. Moreover, while an HHD is described as a remote electronic device used with the inventive bracelet, other devices such as a personal computer having a transponder attached thereto could be used for this purpose. Furthermore, the bracelet need not include printed information. In addition, while conductive loops have been illustrated and described above for absorbing electromagnetic energy and linking a memory to one or more transmitters, it would also be advantageous to provide a loop which traverses the entire length of a bracelet simply to ensure that once the bracelet is cut off one patient it is never again secured to a different patient. To this end, a loop could be configured which, when cut, forms an open circuit in the memory thereby rendering the memory unusable. Additionally, a card reader slot could be incorporated in any of the above embodiments.

Moreover, while the invention is described above as including electrical contacts on the transceiver and the bracelet, clearly the invention should not be so limited. For example, transceiver 200 may be designed to communicate with chip 140 via magnetic coupling wherein transceiver 200 excites chip 140 and, when chip 140 is excited, chip 140 transmits data via an electromagnetic field which is sensed by transceiver 200. Because transceiver 200 and chip 140 are very close when linked, a very small field would be required to excite chip 140 and transmit information back and forth between chip 140 and transceiver 200. Magnetic coupling might be advantageous in that manufacturing tolerances could be reduced as contacts need not be precisely positioned for proper operation. This is particularly advantageous in instances where a transceiver is routinely removed or is used many times thereby subjecting contacts to extreme wear and tear. Thus, the term "contact" is used generically to identify any element which can be linked in any way (e.g. electrically, mechanically, magnetically, through use of light, etc) to another element or contact for exchanging data.

In addition to the operations described above, the present invention contemplates that the inventive apparatus could be used to perform other operations. For example, when a patient is to have a magnetic resonance imaging procedure performed, an imaging machine can query a transceiver to determine if a patient on whom the procedure is about to be performed is the correct patient. If two transceivers are within transmitting distance of the machine, a correct transceiver attached to the patient on whom the procedure is to be performed, both transceivers might respond simultaneously. In this case, several different features might be provided for.

For example, the machine might indicate an error and allow a technician to identify the patient wearing the correct transceiver. In the alternative, the machine might transmit a signal to each transceiver within transmitting range indicating that the correct transceiver should identify itself. Where the correct transceiver is equipped with a light, a visual display or an audio beeper, the correct transceiver could indicate itself by lighting the light, indication on the display, or sounding the beeper.

Moreover, while certain features and inventive aspects have been described above in the context of an assembly wherein the processor is part and parcel to a transceiver and other features have been described above in the context of an assembly wherein the processor is integrally secured to the bracelet such that the processor cannot be removed without damaging the bracelet, any of the features described above may be provided on either of the two assemblies. For example, while a processor which generates an alarm signal when a bracelet is cut was described in the context of the fifth embodiment of the invention including a processor which is integrally secured to the bracelet, clearly, such an alarm signal generating feature could also be provided where the processor is reusable and is part of the transceiver. In this case, the conductive members (1311 and 1313 in FIG. 19) could be linked to the processor through the memory contact/transceiver contact assembly to detect a conductor cut.

In addition, while a "short circuit" for the purposes of identifying a cut bracelet strap has been described as being formed by two separate conductive members which are essentially glued together at their distal ends, a similar suitable conductive member could be formed from a loop conductive member as illustrated in FIG. 14. In this case, assuming the loop extends along essentially the entire length of a strap, when strap ends are secured together any strap cut would necessarily cut the loop conductor. Thus, the term "short circuit" is used in a general sense here and in the claims which follow to mean a circuit wherein, after a strap including a conductor is secured about an object (e.g. a patient's wrist), the strap cannot be cut without cutting the conductor and thereby modifying operation of the device.

Moreover, while the invention has been described as one wherein a bracelet is "securely" fastened about an object (e.g. a wrist) clearly many aspects of the present invention are also applicable to systems wherein a strap or other fastening device is not "securely" fastened to an individual or an object. For example, referring to FIG. 21, an inventive transponder device 2000 may be used with a necklace 2002 in the military or the like wherein the necklace includes a dog-tag 2004 having a memory chip 2006 installed therein. In this case, the transmitter device 2000 would typically not be attached to dog-tag 2004. However, if a person wearing the dog-tag 2004 were admitted to a medical facility, transmitter device 2000 would be attached to tag 2004 to access identification information stored in memory chip 2006 during the stay at the medical facility. In this regard, this embodiment may not include a dog tag and may instead include a memory chip embedded in necklace 2002.

Figures 21, 22:
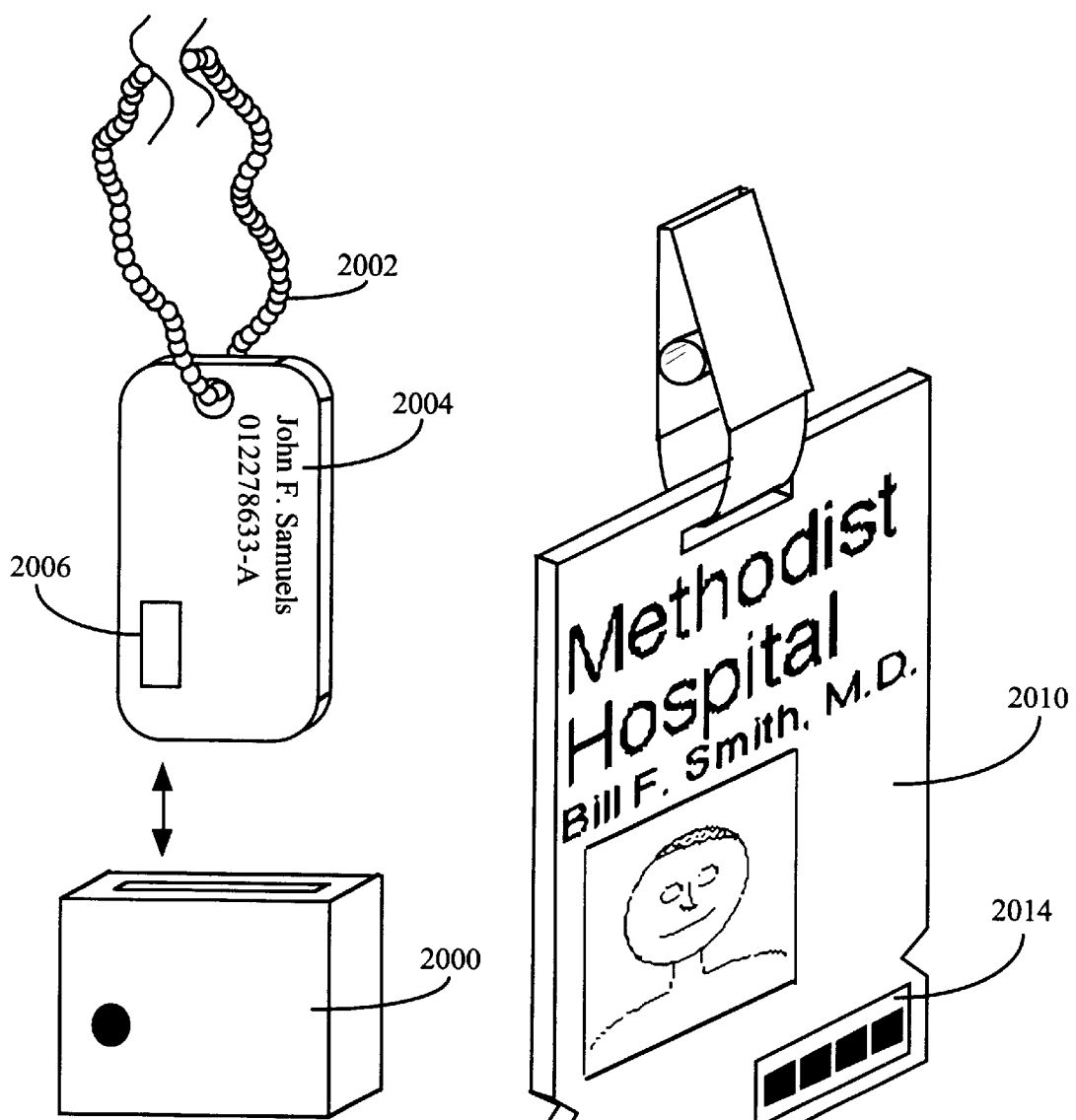
FIG. 21 is a schematic illustrating an inventive necklace including a releasably attached transmitter device.
FIG. 22 is a schematic illustrating an inventive badge including a releasably attached transmitter device.

Similarly, referring to FIG. 22, a removable device may include a badge 2010 which pins onto a person's shirt or the like, a transceiver device 2012 only secured to badge 2010 under certain circumstances such as when an individual enters a particular building where relatively high security might be important. A memory chip 2014 is secured to badge 2010. Other base members for housing hardware having the inventive features are also contemplated (e.g. a belt) and the base members claimed (i.e. strap, necklace, badge) are not meant to be limiting in this regard. In any of the "non-secure" base member or base assembly designs where a transmitter device and memory device may be removed from an individual or an object without damaging the memory device, any of the permutations of the present invention described above, could be employed although some may not make sense with unsecured memory devices. For example, an alarm indicating that a transmitter device has been removed where the base member is a necklace would not make much sense. This is because the purpose of the alarm would be to indicate removal of the transmitter and the entire necklace as a whole could be removed without setting off the alarm by simply removing the entire necklace. Nevertheless, in the case of a badge, badge removal or transmitter device removal from a base member could be indicated via an alarm signal of some type. For example, a clip for securing a badge to a wearer's lapel may be linked to a device processor, the processor recognizing when the clip is opened after being attached to a lapel. Opening could be sensed via a small electrical current passing through the clip, a pressure sensor or so on. The opening of clip can be used as a signal, as previously described for the sixth embodiment, for the processor to perform any of the functions mentioned above regarding erasing memory chip 140, no longer transferring memory contents, and presenting an alarm signal.

In addition to the applications described above, the invention may also be used in other useful medical applications. For example, where a mother gives birth to an infant and the mother has an identification device attached to her wrist, at the time of birth, it is contemplated that an identification device would be attached to the child's wrist also. To insure that there is no mix up between children when the newborn child is taken to the facility nursery at the time of birth, it is contemplated that at the time of birth the mother's identification device could be activated to first identify the time of birth via a processor clock and thereafter to transmit the mother's name and perhaps other identification information and the specific time of birth to the infant's identification device. In addition, the mother's device would store the time of birth in an associated device memory. In this manner, assuming the infant's bracelet is not removed, the mother's information and the specific time of birth would clearly identify the baby as being related to the specific mother at subsequent times. By measuring time in microseconds and having each processor clock being able to set to only within a minute of time in precision, the time recorded in the baby's bracelet is effectively a secret random number only recorded in the memory of the two bracelets, ensuring the number cannot be guessed.

A similar feature is also contemplated where, due to prolonged facility occupancy, an identification strap has to be replaced (e.g. the original strap is soiled). In this case, it is contemplated that a first identification device could be linked to a strap on the patient and a second identification device could be linked to a new strap. Thereafter, the first device could be activated to transmit all data on the first strap memory to the second device, the second device thereafter storing all of the transferred data on the memory of the second strap.

Furthermore, while the invention is described above as one where an HHD is used to interrogate an identification device, other systems or devices are contemplated which result in additional and advantageous synergistic results. For example, it is contemplated that each facility room will include one or more monitoring devices for monitoring identification devices in the room. The monitoring device may be secured at a central ceiling location. In one embodiment, the monitoring device may be able to interrogate and also receive identifying information. In this case, it is contemplated that the monitoring device may periodically (e.g. every second) query each identification device in a room, thereafter receiving an identification signal from each device in the room. In another embodiment, each identifying device in a room my be programmed to periodically (e.g. every second) send an identifying signal to the monitoring device to indicate presence and correct operation of the identifying device.

In either of the embodiments described (i.e. where the monitoring device interrogates and where the identifying device autonomously sends identifying signals), a simple and relatively inexpensive security system can be devised. For example, in the case of a facility nursery where a plurality (e.g. 10) of infants are kept, the monitoring device and separate identification devices on each infant may be programmed to detect when an infant is removed from the nursery and/or when an identification device is rendered inoperable. In this case, where the monitoring device expects an identification signal from an identification device and does not receive the expected signal, the monitoring device can be programmed to indicate lack of the signal.

In a particularly advantageous security application, identification devices like the device illustrated in FIG. 15 which includes a transmitter, an rf antenna and memory integrally secured to a strap are used with an rf power source and a monitoring device. In this case, the rf source provides power to the identification devices, the identification devices in turn transmitting identification signals to the monitoring devices. This embodiment is advantageous as the identification devices can be made extremely light-weight.

Moreover, while the fasteners described above include mechanical fasteners, chemical fasteners such as adhesives may also be used to affix a base member to an object or the like. For example, in one embodiment the base member may be a label for a medication container or dispenser which includes adhesive on one side of the label and includes a memory device embedded in or attached securely to the label. Such an example is described and illustrated in detail in U.S. patent application Ser. No. 08/832,613 which was filed on Mar. 28, 1997 and is entitled "Interactive Label For Medication Containers and Dispensers" and was filed by the present inventor. In another embodiment, referring to FIG. 11 of the present application, instead of being attached to a strap 112, the tracks 404 and memory device associated therewith and positioned therebetween (i.e. the device located generally at position 120) and referred to hereinafter as device 120, device 120 may be securely attached via an adhesive to a box or package, the memory storing information associated with the content of the box or package. In this case, a transceiver 420 could be attached to the package or box temporarily via tracks 404 and could be used to identify the content of the box or package electronically. Thus, in this context the term "fastener" has an extremely broad meaning including chemical as well as mechanical attachment means.

Furthermore, referring to FIGS. 32 and 33, while the embodiment therein teaches base member or fastener 2372 secured to vessel container 2362, base member 2370 could be secured to the closure member or lid 2364. Similarly, while latch solenoid 2384 is shown integral with processor assembly or transceiver 2380, latch 2384 may be integral with base member 2370, lid 2364 or container 2362 so long as solenoid 2384 is controllable by the transceiver processor (not illustrated in FIG. 32) when lid 2364 is closed and transceiver 2380 is secured to base member 2370 and solenoid 2384 is juxtaposed with respect to other assembly components so that when the solenoid is extended lid 2364 is locked.

Moreover, while a mechanical lock is illustrated in FIGS. 32 and 33, other lock types are contemplated such as a magnetic locking device.

To apprize the public of the scope of this invention, I make the following claims:

I claim:

1. An electronic identification apparatus for identifying an object, the apparatus comprising:

a base member having a connector for attaching the base member to the object;

a processor assembly attached to the base member and including:

a memory for storing data;

a sensor for sensing when the processor assembly is linked to the object; and a processor linked to the memory and the sensor, the sensor indicating to the processor whether or not the processor assembly is linked to the object, the processor performing at least one security function when the processor assembly is de-linked from the object.

2. The apparatus of claim 1 wherein the processor assembly further includes a transponder linked to the processor.

3. The apparatus of claim 2, wherein the base member is a strap having first and second end segments and is capable of assuming a secured configuration wherein the first and second end segments are adjacent and the strap forms a loop around the object, a conductive lead extends from the first to the second end segments, the processor assembly further including first and second conductive leads, the first end segment being coupled to the first conductive lead and the second end segment being coupled to the second conductive lead to form a loop.

4. The apparatus of claim 3, further comprising a plurality of transponders spaced along the loop and linked to the processor assembly.

5. The apparatus of claim 3, further comprising a plurality of indicators spaced along the loop and linked to the processor assembly.

6. The apparatus of claim 1, wherein the sensor is selected from a group consisting of a pressure sensor, photoelectric sensor and a magnetic sensor.

7. The apparatus of claim 1, wherein the sensor comprises at least one electrical terminal of the processor assembly positioned to contact at least one corresponding electrical terminal of the base member when the processor assembly is attached to the base member.

8. The apparatus of claim 1, wherein the at least one security function includes clearing the memory contents.

9. The apparatus of claim 1, wherein the processor assembly further includes one of an audible alarm, an rf alarm and a visual alarm linked to the processor.

10. The apparatus of claim 9, wherein the processor assembly is removably attached to the base member and the security function includes activating the alarm when the processor assembly is removed from the base member.

11. The apparatus of claim 10, wherein the processor inhibits the alarm when a disable signal is received.

12. The apparatus of claim 11, wherein the processor assembly includes a transponder having a receiver and the apparatus is to be used with an external control device, the control device providing the disable signal to the processor via the transponder.

13. The apparatus of claim 1, wherein the processor assembly further includes a display linked to the processor for visually presenting at least a subset of the memory contents.

14. The apparatus of claim 13, wherein the at least one security function includes suppressing the display of the memory contents.

15. The apparatus of claim 1, wherein the at least one security function includes disabling the memory.

16. The apparatus of claim 15, wherein the processor assembly includes a transponder having a receiver for receiving control signals from at least one external control device and, wherein, the at least one security function includes, after disabling the memory, when an access code is received from the at least one control device via the receiver, enabling the memory.

17. The apparatus of claim 16, wherein the external control device is a hand-held computing device.

18. The apparatus of claim 2, wherein the transponder includes a receiver linked to the processor for receiving data for storage in the memory.

19. The apparatus of claim 1, further including at least one sensing transducer linked to the processor for collecting data for storage in the memory, wherein the collected data relates to at least one of the object and the object's environment.

20. The apparatus of claim 19, wherein the processor assembly includes a transponder having a transmitter for transmitting the collected data and the basic identification information from the memory, the collected data being transferred only in association with the basic identification information.

21. The apparatus of claim 19, wherein the collectible data types include pulse rate, temperature, pressure, pulse oximetry and cardio-diagnostic measurements, and the transducer collects data of at least one of the collectible data types.

22. The apparatus of claim 2, wherein the transponder includes a transmitter for transmitting at least a sub-set of the data stored in the memory.

23. The apparatus of claim 22, wherein the at least one security function includes disabling the transmitter.

24. The apparatus of claim 19, wherein the apparatus is also for use with external devices, the transponder further including a receiver linked to the processor for receiving data from at least one external device, the processor storing in the memory at least a subset of data received from an external device.

25. The apparatus of claim 24 wherein basic object identification information identifying the object stored in the memory and the received data is stored in association with the basic identification information.

26. The apparatus of claim 24, wherein the at least one function includes disabling one of the transmitter and the receiver.

27. The apparatus of claim 26, wherein, if the security function is to disable the transmitter, the security function further includes, after disabling the transmitter, when an access code is received from at least one external device via the receiver, enabling the transmitter.

28. The apparatus of claim 27, wherein the processor assembly also includes an enabling component linked to the processor and, if the security function is to disable the receiver, when the receiver is disabled the function further includes monitoring the enabling component for an access code and when a code is received, re-enabling the receiver.

29. The apparatus of claim 1, wherein the processor assembly is contained in a housing having a first latch device, the base member includes a second latch device, and the first and second latch devices are configured such that the processor assembly can be connected and disconnected to the base member.

30. The apparatus of claim 29, wherein the sensor also senses when the processor assembly is disconnected from the base member.

31. The apparatus of claim 30, wherein the sensor is a first sensor and the base member further includes a second sensor for sensing then the base member is disconnected from the object, when the processor assembly is connected to the base member, the second sensor is linked to the processor such that the processor also monitors connecting and disconnecting of the base member to the object, the processor performing at least one security function when the base member is disconnected from the object and the processor is connected to the base member.

32. The apparatus of claim 31, wherein the at least one security function is one of disabling the memory and clearing the memory.

33. The apparatus of claim 31, wherein the processor assembly further includes an alarm linked to the processor, wherein the at least one security function includes activating the alarm.

34. The apparatus of claim 31, wherein the processor assembly further includes a clock, wherein the at least one security function includes recording in the memory the time the processor assembly was disconnected from the object.

35. The apparatus of claim 31, wherein the processor assembly further includes a transmitter and the at least one security function includes disabling the transmitter.

36. The apparatus of claim 1, wherein the at least one security function includes retaining the contents of the memory until the processor assembly is attached to one of another object and another base member at which point the memory is cleared.

37. The apparatus of claim 31, wherein the base member is a strap.

38. The apparatus of claim 37, wherein the second sensor includes at least one conductive member within the strap which forms at least a portion of a conductive loop about the object when attached to the object.

39. The apparatus of claim 38, wherein the strap includes first and second end segments and is capable of assuming a second configuration wherein the first and second end segments are adjacent and the strap forms a loop around the object, the conductive lead extending from the first to the second end segments, the processor assembly further including first and second conductive leads, the first end segment being coupled to the first conductive lead and the second end segment being coupled to the second conductive lead to form a loop.

40. The apparatus of claim 39, wherein the second end segment is connectable to the second conductive lead via an adhesive.

41. The apparatus of claim 1, wherein the connector is an adhesive.

42. The apparatus of claim 41, wherein the at least one security function is one of disabling the memory and clearing the memory.

43. The apparatus of claim 41, wherein the processor assembly further includes an alarm linked to the processor, wherein the at least one security function includes activating the alarm.

44. The apparatus of claim 41, wherein the processor assembly further includes a clock, wherein the at least one security function includes recording in the memory the time the processor assembly was disconnected from the object.

45. The apparatus of claim 41, wherein the processor assembly further includes a transmitter, wherein the at least one security function includes disabling the transmitter.

46. The apparatus of claim 41, wherein the at least one security function includes retaining the contents of the memory until the processor assembly is attached to one of another object and another base member at which point the memory is cleared.

47. The apparatus of claim 1, wherein the sensor is a pressure sensor including at least one resilient extension member capable of assuming a relaxed position and a flexed position, the sensor indicating detachment when the extension member is in the relaxed position, and wherein the base member and processor assembly further include first and second latch devices which cooperate to releasably attach the processor assembly to the base member, at least on of the object and a latch device forming a pressure surface, the latch devices, extension member and pressure surface configured such that when the processor assembly is attached to the base member the extension member is forced into the flexed position by the pressure surface.

48. The apparatus of claim 47, wherein the pressure surface is formed by the object.

49. The apparatus of claim 2, wherein the transponder is capable of communication via radio frequency signals.

50. The apparatus of claim 1, wherein the processor assembly further comprises a clock linked to the processor.

51. The apparatus of claim 49, wherein the at least one security function includes recording the approximate time processor was disconnected from the object.

52. The apparatus of claim 1, wherein the object includes a container vessel and a closure member, the vessel having an opening which is closable via the closure member when the closure member is in a closed position, the apparatus further including a latching device attached to one of the base member, the vessel, the closure member and the processor assembly, the latching device capable of assuming each of a locked and an unlocked state, when the closure member is in the closed position and the processor assembly is attached to the base member, the processor assembly is linked to the latching device for controlling the latching device, the latching device is juxtaposed with respect to the closure member, the vessel and the base member such that when the latching device is in the locked state, the closure member is locked in the closed position and, when the latching device is in the unlocked state, the closure member can be removed to open the vessel.

53. The apparatus of claim 1, wherein the at least one security function includes retaining the contents of the memory until the processor assembly is attached to one of another object and another base member, at which point the memory is cleared.

54. An electronic identification apparatus for identifying an object, the apparatus comprising:
a base member having a connector for connecting the base member to the object;
a processor assembly attached to the base member and including:
a memory for storing data;
a transponder;
a sensor for sensing when the processor assembly is connected to the object; and
a processor linked to the memory, the transponder and the sensor, the sensor indicating to the processor whether or not the processor assembly is connected to the object, the processor performing at least one security function when the processor assembly is disconnected from the object;
wherein the at least one security function includes at least one of clearing the memory, disabling the memory and disabling the transponder.

55. The apparatus of claim 54, wherein the base member is a strap having first and second end segments and is capable of assuming a second configuration wherein the first and second end segments are adjacent and the strap forms a loop around the object, a conductive lead extends from the first to the second end segments, the processor assembly further including first and second conductive leads, the first end segment being coupled to the first conductive lead and the second end segment being coupled to the second conductive lead to form a loop.

56. The apparatus of claim 55, further comprising a plurality of transponders spaced along the loop and linked to the processor assembly.

57. The apparatus of claim 55, further comprising a plurality of indicators spaced along the loop and linked to the processor assembly.

58. The apparatus of claim 54, wherein the sensor is selected from a group consisting of a pressure sensor, a photoelectric sensor and a magnetic sensor.

59. The apparatus of claim 54, wherein the sensor comprises at least one electrical terminal of the processor assembly positioned to contact at least one corresponding electrical terminal of the base member when the processor assembly is attached to the base member.

60. The apparatus of claim 54, wherein the processor assembly further includes one of an audible alarm, an rf alarm and a visual alarm linked to the processor.

61. The apparatus of claim 60, wherein the at least one security function further includes activating an alarm when said processor assembly is removed from the object.

62. The apparatus of claim 61, wherein the processor inhibits the alarm when a disable signal is received.

63. The apparatus of claim 62, wherein the transponder includes a receiver and the apparatus is to be used with an external control device, the control device providing the disable signal to the processor via the receiver.

64. The apparatus of claim 54, wherein the processor assembly further includes a display linked to the processor for visually presenting at least a subset of the memory contents.

65. The apparatus of claim 64, wherein the at least one security function includes suppressing the display of the memory contents.

66. The apparatus of claim 54, wherein the transponder includes a receiver for receiving control signals from at least one external control device, and wherein, if the at least one security function is to disable the memory, the security function further includes, after disabling the memory, when an access code is received from the at least one control device via the receiver, enabling the memory.

67. The apparatus of claim 66, wherein the external control device is a hand-held computing device.

68. The apparatus of claim 54, wherein the transponder includes a receiver linked to the processor for receiving data for storage in the memory.

69. The apparatus of claim 54, further including at least one sensing transducer linked to the processor for collecting data for storage in the memory, wherein the collected data relates to at least one of the object and the object's environment.

70. The apparatus of claim 69, wherein the transponder includes a transmitter for transmitting at least a sub-set of the data stored in the memory.

71. The apparatus of claim 69, wherein the object is a patient, the collectible data types include pulse rate, temperature, pressure, pulse oximetry and cardio-diagnostic measurements, and the transducer collects data of at least one of the collectible data types.

72. The apparatus of claim 54, wherein at least basic identification information identifying the patient is stored in the memory and the transponder includes a transmitter for transmitting at least the basic identification information from the memory.

73. The apparatus of claim 72, wherein the apparatus is also for use with external devices, the transponder further including a receiver linked to the processor for receiving data from at least one external device, the processor storing in the memory at least a subset of data received from an external device.

74. The apparatus of claim 73, wherein the received data is stored in association with the basic identification information.

75. The apparatus of claim 54, wherein, the processor assembly includes an enabling component and, if the security function is to disable the transponder, the at least one security function further includes, after disabling the transponder, when an access code is received from at least one external device via the enabling component, enabling the transponder.

76. The apparatus of claim 54, wherein the processor assembly is contained in a housing having a first latch device, the base member includes a second latch device, and the first and second latch devices are configured such that the processor assembly can be connected and disconnected to the base member.

77. The apparatus of claim 76, wherein the sensor senses when the processor assembly is disconnected from the base member.

78. The apparatus of claim 77, wherein the sensor is a first sensor and the base member further includes a second sensor for sensing then the base member is disconnected from the object, when the processor assembly is connected to the base member, the second sensor is linked to the processor such that the processor also monitors connecting and disconnecting of the base member to the object, the processor performing at least one security function when the base member is disconnected from the object and the processor is connected to the base member.

79. The apparatus of claim 78, wherein the processor assembly further includes an alarm linked to the processor, wherein the at least one security function includes activating the alarm.

80. The apparatus of claim 78, wherein the processor assembly further includes a clock, wherein the at least one security function includes recording in the memory the time the processor assembly was disconnected from the object.

81. The apparatus of claim 78, wherein the at least one security function includes retaining the contents of the memory until the processor assembly is attached to one of another object and another base member at which point the memory is cleared.

82. The apparatus of claim 78, wherein the base member is a strap.

83. The apparatus of claim 82, wherein the second sensor includes at least one conductive member within the strap which forms at least a portion of a conductive loop about the object when attached to the object.

84. The apparatus of claim 83, wherein the strap is detachable from the object only via cutting the conductive member.

85. The apparatus of claim 84, wherein the strap includes first and second end segments and is capable of assuming a second configuration wherein the first and second end segments are adjacent and the strap forms a loop around the object, the conductive lead extending from the first to the second end segments, the processor assembly further including first and second conductive leads, the first end segment being coupled to the first conductive lead and the second end segment being coupled to the second conductive lead to form a loop.

86. The apparatus of claim 84, wherein the second end segment is connectable to the second conductive lead via an adhesive.

87. The apparatus of claim 54, wherein the connector is an adhesive.

88. The apparatus of claim 87, wherein the processor assembly further includes an alarm linked to the processor, wherein the at least one security function includes activating the alarm.

89. The apparatus of claim 87, wherein the processor assembly further includes a clock, wherein the at least one security function includes recording in the memory the time the processor assembly was disconnected from the object.

90. The apparatus of claim 87, wherein the at least one security function includes retaining the contents of the memory until the processor assembly is attached to one of another object and another base member at which point the memory is cleared.

91. The apparatus of claim 58, wherein the sensor is a pressure sensor including at least one resilient extension member capable of assuming a relaxed position and a flexed position, the sensor indicating detachment when the extension member is in the relaxed position, and wherein the base member and processor assembly further include first and second latch devices which cooperate to releasably attach the processor assembly to the base member, at least on of the object and a latch device forming a pressure surface, the latch devices, extension member and pressure surface configured such that when the processor assembly is attached to the base member the extension member is forced into the flexed position by the pressure surface.

92. The apparatus of claim 44, wherein the pressure surface is formed by the object.

93. The apparatus of claim 54, wherein the transponder is capable of communication via radio frequency signals.

94. The apparatus of claim 54, wherein the processor assembly is integrally linked to the base member and the sensor senses when the base member is disconnected from the object.

95. The apparatus of claim 94, wherein the processor assembly can be removed from the object only in a tamper evident manner.

96. The apparatus of claim 94, wherein the base member is a strap.

97. The apparatus of claim 96, wherein the sensor includes at least one conductive member in the strap which, when the strap is secured to the object, loops around the object and wherein the strap cannot be removed from the object without cutting the conductive member.

98. The apparatus of claim 97, wherein the transponder includes a transmitter for transmitting at least a sub-set of the information in the memory and the at least one security function includes disabling the transmitter.

99. The apparatus of claim 54, wherein the processor assembly further comprises a clock linked to the processor.

100. The apparatus of claim 99, wherein the at least one security function includes recording the approximate time the processor assembly is disconnected from the object.

101. The apparatus of claim 54, wherein the object includes a container vessel and a closure member, the vessel having an opening which is closable via the closure member when the closure member is in a closed position, the apparatus further including a latching device attached to one of the base member, the vessel, the closure member and the processor assembly, the latching device capable of assuming each of a locked and unlocked state, when the closure member is in the closed position and the processor assembly is attached to the base member, the processor assembly is linked to the latching device for controlling the latching device, the latching device is juxtaposed with respect to the closure member, the vessel and the base member such that when the latching device is in the locked state, the closure member is locked in the closed position and, when the latching device is in the unlocked state, the closure member can be removed to open the vessel.

102. The apparatus of claim 94, wherein the processor assembly can be removed from the object only in a tamper evident manner.

103. An electronic information apparatus for use with an object data device that stored information related to an object, the apparatus comprising:
 (A) a base member having a connector for attaching the identification apparatus to the object; and
 (B) a processor assembly including:
  (1) a housing linkable to the base member;
  (2) a memory for storing information;
  (3) a data reader for reading information from an object data device; and
  (4) a processor linked to the memory and the reader for receiving information from the reader and storing the information in the memory.

104. The apparatus of claim 103, wherein the object data device is a data card including an interface segment, the reader capable of reading data via the interface segment.

105. The apparatus of claim 104, wherein the object is a person and the object data device information is selected from the group consisting of name, age, birth date, height, weight, hair color, eye color, and identification number.

106. The apparatus of claim 104, wherein the interface segment is a first electronic contact and the reader includes a second electronic contact and wherein, when the first and second contacts make contact, the reader is capable of reading the data.

107. The apparatus of claim 104, wherein the interface segment is a magnetic strip and the reader is a magnetic strip reader.

108. The apparatus of claim 104, wherein the housing form a pass-through slot for receiving at least a portion of the card, the reader positioned within the slot such that, as the card is placed therein, the reader is adjacent the interface segment.

109. The apparatus of claim 103, wherein the base member is a strap having first and second end segments and capable of assuming a secured configuration wherein the first and second end segments are adjacent and the strap forms a loop around the object.

110. The apparatus of claim 103, wherein once information pertaining to the object is read from the data device, the processor disables the reader until the processor receives a special code.

111. The apparatus of claim 110, wherein the processor assembly further includes a receiver and is also for use with at least one external control device, wherein the special code is received by the processor via the receiver from the control device.

112. The apparatus of claim 103, wherein the processor assembly further includes a transmitter linked to the processor for transmitting data stored in the memory.

113. The apparatus of claim 112, wherein data stored in the memory includes basic identification information identifying the object and the transmitted data includes the basic identification information.

114. The apparatus of claim 112, wherein the processor assembly is removably secured to the base member.

115. The apparatus of claim 1 14, wherein the processor assembly further includes a sensor for sensing when the processor assembly is removed from the object and wherein, when the assembly is removed, the processor performs at least on security function.

116. The apparatus of claim 115, wherein the at least one security function is one of disabling the memory and clearing the memory.

117. The apparatus of claim 115, wherein the processor assembly further includes an alarm linked to the processor, wherein the at least one security function includes activating the alarm.

118. The apparatus of claim 31, wherein the processor assembly further includes a clock, wherein the at least one security function includes recording in the memory the time the processor assembly was disconnected from the object.

119. The apparatus of claim 115, wherein the processor assembly further includes a transponder, wherein the at least on security function includes disabling the transponder.

120. The apparatus of claim 115, wherein the at least one security function includes retaining the contents of the memory until the processor assembly is attached to one of another object and another base member at which point the memory is cleared.

121. The apparatus of claim 115, wherein the processor assembly further includes a sensing transducer linked to the processor for collecting data regarding the object for storage in the memory.

122. The apparatus of claim 121, wherein the transmitter can be used to transmit the collected data and the basic identification information in the memory, the collected data being transferred only in association with the basic identification information.

123. The apparatus of claim 103, wherein the processor assembly further includes a receiver for receiving data from other devices for storage in the memory.

124. The apparatus of claim 103, wherein the processor assembly further comprises a clock linked to the processor.

125. The apparatus of claim 124, wherein the at least one security function includes recording the approximate time the processor was disconnected from the object.

126. The apparatus of claim 103, wherein the object includes a container vessel and a closure member, the vessel having an opening which is closable via the closure member when the closure member is in a closed position, the apparatus further including a latching device attached to one of the base member, the vessel, the closure member and the processor assembly, the latching device capable of assuming each of a locked and unlocked state, when the closure member is in the closed position and the processor assembly is attached to the base member, the processor assembly is linked to the latching device for controlling the latching device, the latching device is juxtaposed with respect to the closure member, the vessel and the base member such that when the latching device is in the locked state, the closure member is locked in the closed position and, when the latching device is in the unlocked state, the closure member can be removed to open the vessel.

127. The apparatus of claim 103, wherein the processor assembly can be removed from the object only in a tamper evident manner.

128. The apparatus of claim 103, wherein the base member is a strap having first and second end segments and is capable of assuming a configuration wherein the first and second end segments are adjacent and the strap forms a loop around the object, the conductive member extending from the first to the second end segments, the processor assembly further including first and second conductive leads, the first end segment being coupled to the first conductive lead and the second end segment being coupled to the second conductive lead to form a loop.

129. The apparatus of claim 128, further comprising a plurality of transponders spaced along the loop and linked to the processor assembly.

130. The apparatus of claim 128, further comprising a plurality of indicators spaced along the loop and linked to the processor assembly.

131. A contents identifying containment apparatus comprising:
(A) a vessel forming a container volume having an opening
(B) a closure member for closing the opening;
(C) a base member affixed to one of the vessel and the closure member having at least one latching device extending;
(D) a memory for storing information
(E) a processor assembly having:
(1) a housing including a second latching device configured so as to receivable by the first latching device to secure the processor assembly to the base member; and
(2) a processor linked to the memory for processing container control information, the processor assembly, vessel, closure member and base member each being apparatus components; and
(F) a latch linked to one of the apparatus components and when the housing is attached to the base member, positioned with respect to the vessel so as to restrain the closure member when in a lock position and to allow the closure member to be moved when in an unlock position;
wherein, when the housing is attached to the base member, the processor is linked to the latch for controlling the latch.

132. The apparatus of claim 131, wherein the memory is integral with the base member.

133. The apparatus of claim 131, wherein the memory is a part of the processor assembly.

134. The apparatus of claim 131, wherein the processor assembly further includes an input device for receiving information related to the container vessel contents.

135. The apparatus of claim 131, wherein the latch is a solenoid.

136. The apparatus of claim 135, wherein the closure member is one of a hinged lid, a threaded lid and a fit-on lid, the solenoid being positioned so as to restrain the closure member when in the locked position.

137. The apparatus of claim 134, wherein the processing assembly is removably attached to the base member and wherein the base member and the housing have corresponding conductive terminals that are in physical contact when the processing assembly is attached to the base member, the housing terminals being linked to the processor.

138. The apparatus of claim 134, wherein the input device is an input-output connector for receiving and sending the container content information via conductive lead.

139. The apparatus of claim 138, wherein the container content information is sent only in association with the basic identification information.

140. The apparatus of claim 134, wherein the input device is a transponder for receiving and transmitting container content information wirelessly.

141. The apparatus of claim 131, wherein the processor assembly further includes a sensor linked to the processor for detecting whether the processor assembly is connected to the container vessel, the processor performing at least one security function when the processing assembly is removed from the container.

142. The apparatus of claim 141, wherein the at least one security function is on of disabling the memory and clearing the memory.

143. The apparatus of claim 141, wherein the processor assembly further includes an alarm linked to the processor, wherein the at least one security function includes activating the alarm.

144. The apparatus of claim 141, wherein the processor assembly further includes a clock, wherein the at least one security function includes recording in the memory the time the processor assembly was disconnected from the container vessel.

145. The apparatus of claim 141, wherein the processor assembly further includes a transponder, wherein the at least one security function includes disabling the transponder.

146. The apparatus of claim 141, wherein the at least one security function includes retaining the contents of the memory until the processor assembly is attached to one of another container vessel and another base member, at which point the memory is cleared.

147. The apparatus of claim 131, wherein the latch is operated according to container control information stored in the memory.

148. The apparatus of claim 131, wherein the latch is operated according to container control information received from an external control device.

149. The apparatus of claim 131, wherein the processor assembly further comprises a clock linked to the processor.

150. The apparatus of claim 131, wherein the processor assembly can be removed from the container vessel only in a tamper evident manner.

151. An electronic identification apparatus for identifying an object, comprising:
a base member having a connector for attaching the base member to the object;
at least one sensing transducer linkable to an external device containing data and, when an external device is linked, collecting data from the external device; and
a memory attached to the base member and linked to the sensing transducer, the memory storing the data collected from the external device.

152. The apparatus of claim 151, wherein the base member is a strap having first and second end segments and capable of assuming a secured configuration wherein the first and second end segments are adjacent and the strap forms a loop around the object.

153. The apparatus of claim 152, wherein the apparatus includes a sensor for detecting whether the base member is connected to the object, the apparatus performing at least one security function when the base member is disconnected from the object.

154. The apparatus of claim 153, wherein the at least one security function is one of disabling the memory and clearing the memory.

155. The apparatus of claim 153, wherein the processor assembly further includes an alarm linked to the processor, wherein the at least one security function includes activating the alarm.

156. The apparatus of claim 153, wherein the processor assembly further includes a clock, wherein the at least one security function includes recording in the memory the time the processor assembly was disconnected from the object.

157. The apparatus of claim 153, wherein the processor assembly further includes a transponder, wherein the at least one security function includes disabling the transponder.

158. The apparatus of claim 153, wherein the at least one security function includes retaining the contents of the memory until the processor assembly is attached to one of another object and another base member, at which point the memory is cleared.

159. The apparatus of claim 153, wherein the processor assembly further comprises a clock.

160. The apparatus of claim 159, wherein the at least one security function includes recording the approximate time the base member was disconnected from the object.

161. The apparatus of claim 160, wherein the base member can be removed from the object only in a tamper evident manner.

162. A method of using an electronic identification device for identifying an object, the device having a base member connected to the object, a processor assembly connected to the base member such that the processor assembly can be removed from and reconnected to the object, the processor assembly including a memory, a sensor for sensing when the processor assembly is connected to the object, and a processor linked to the memory and the sensor, the method comprising the steps of:
(A) monitoring, with the sensor, whether the processor assembly is connected to the base member; and
(B) when the sensor indicates the processor assembly is disconnected from the base member, performing at least one security function.

163. A method of using an electronic identification device attached to an object and capable of acquiring object related information from an object data device having readable segment, the electronic identification device having a processor assembly including a processor, a connection sensor, a memory and a data reader for reading information from the object data device, the processor being linked to the sensor, the memory, the method comprising the steps of:
(A) reading information from the object data device with the reader of the processor assembly, the information at least including basic identification information;
(B) storing at least the basic identification information in the memory;
(C) monitoring, with the sensor, whether the processor assembly is connected to the object; and
(D) when the sensor indicates the processor assembly is disconnected from the object, performing at least one security function.

164. The method of using a contents identifying containment apparatus comprising a closable container vessel to which is affixed a memory and a processor linked to the memory, the container vessel also having a latch linkable to the processor and positioned so as to control opening and closing of the container vessel, the method comprising the steps of:
(A) storing in the memory basic identification information pertaining to the contents of the container vessel;
(B) receiving container control information; and
(C) when the container is closed, operating the latch to extend to a locked position so as to prevent the container from being opened and to retract to an unlocked position to allow the container to be opened, the latch being under the control of the processor assembly and operated according to the container control information.

165. The method of claim 164, further comprising the steps of:
(D) monitoring, with the sensor, whether the processor assembly is connected to the container vessel; and
(E) when the sensor indicates the processor assembly is disconnected from the container vessel, performing at least one security function.

* * * * *